United States Patent [19]
Andersson et al.

[11] Patent Number: 5,430,057
[45] Date of Patent: Jul. 4, 1995

[54] PARENTERAL BUSULFAN FOR TREATMENT OF MALIGNANT DISEASE

[75] Inventors: Borje S. Andersson; Harshal P. Bhagwatwar; Diana S. L. Chow, all of Houston, Tex.

[73] Assignees: Board of Regenth, The University of Texas System, Austin; University of Houston-University Park, Houston, both of Tex.

[21] Appl. No.: 129,995

[22] Filed: Sep. 30, 1993

[51] Int. Cl.[6] ........................................ A61K 31/255
[52] U.S. Cl. ................................................ 514/517
[58] Field of Search .......................... 514/517; 558/61

[56] References Cited

FOREIGN PATENT DOCUMENTS 2501675 9/1982 France .
92/02256 2/1992 WIPO .

OTHER PUBLICATIONS

Medication Package Insert for Methotrexate, Lederle. 1992.
Giles et al., "A Platelet Release Defect Induced by Aspirin or Penicillin G Does Not Increase Gastrointestinal Blood Loss in Thrombocytopenic Rabbits," *Haematology*, vol. 57, No. 1, 1984, pp. 17-23.
Bhagwatwar et al., "*In Vitro* and *In Vivo* Evaluations of Intravenous Busulfan Formulation," *Pharmaceutical Research*, vol. 10, No. 10, Oct. 1993, p. S190.
Harshal et al., "Development of Intravenous Formulation of Busulfan," *Pharmaceutical Research*, vol. 9, No. 10, 1992, p. S200.
J. E. F. Reynolds, "Busulfan," *Martindale, The Extra Pharmacopoeia*, 1989, The Pharmaceutical Press, London, pp. 603-604.
Bhagwatwar, et al., "Formulation and Pharmacokinetics of Intravenous (I.V.) Busulphan," *Proceedings of the American Association for Cancer Research*, vol. 34, Mar. 1993, p. 269.
Hagihara, *Database WPI*, Week 8916, Derwent Publications Ltd., London, GB; AN 89-117247 * JP, A, 1 061 429 8 Mar. 1989 see abstract.
Andersson et al., "*In Vitro* and *In Vivo* Evaluations of Intravenous Busulfan Formulation," *American Assoc. of Clinical Pharmacists*, Annual Meeting, Nov. 1993. Abstract only.
Bhagwatwar et al., "Formulation and Pharmacokinetics of Intravenous (I.V.) Busulphan (BU) in the Rat," *American Association for Cancer Research*, Orlando, Florida meeting, May 19-23, 1993. Abstract only.
Blaise et al., "A Randomized Study OD CY-TBI vs BUS-CY+ALLO BMT for ANL in First CR: A Gegmo Study," *BMT Suppl.*, 26, 1990, Abstract only.
Buckner et al., "A Randomized Study Comparing Two Transplant Regimens for CML in Chronic Phase (CP)," *Blood*, 80(10) (Suppl. 1):277, 1992. Abstract only.
Copelan et al., "Marrow Transplantation Following Busulfan and Cyclophosphamide for Chronic Myelogenous Leukaemia in Accelerated or Blastic Phase," *British Journal of Haematology*, 71:487-491, 1989.
Giles et al., "A Platelet Release Defect Induced by Aspirin or Penicillin G Does Not Increase Gastrointestinal Blood Loss in Thrombocytopenic Rabbits," *British Journal of Haematology*, 57(1):17-23, 1984. Abstract only.
Grochow et al., "Busulfan Disposition in Children," *Blood*, 75(8):1723-1727, 1990.
Grochow et al., "Pharmacokinetics of Busulfan: Correlation with Veno-Occlusive Disease in Patients Undergoing Bone Marrow Transplantation," *Cancer Chemotherapy and Pharmacology*, 25:55-61, 1989.
Hagenbeek, A., "Introduction of the BN Myelocytic Leukaemia," *Leukemia Research*, 1:85-90, 1977.
Hagenbeek et al., "Proliferation Kinetics of the BNML (List continued on next page.)

*Primary Examiner*—Raymond Henley, III
*Assistant Examiner*—Phyllis G. Spivack
*Attorney, Agent, or Firm*—Arnold, White & Durkee

[57] ABSTRACT

Stable parenteral formulations of busulfan safe for parenteral administration are disclosed that exhibit improved bioavailability and optimize high dose busulfan therapy against malignant disease.

31 Claims, 10 Drawing Sheets

Leukaemia *In Vivo,*" *Leukemia Research,* 1(2/3):99–101, 1977.

Hassan et al., "Cerebrospinal Fluid and Plasma Concentrations of Busulfan During High-Dose Therapy," *Bone Marrow Transplantation,* 4:113–114, 1989.

Hassan et al., "Pharmacokinetics of High-Dose Busulphan in Relation to Age and Chronopharmacology," *Cancer Chemotherapy and Pharmacology,* 28:130–134, 1991.

Hassan et al., "*In Vivo* Distribution of [$^{11}$C]–Busulfan in *Cynomolgus Monkey* and in the Brain of a Human Patient," *Cancer Chemotherapy and Pharmacology,* 30:81–85, 1992.

Hassan et al., "Pharmacokinetic and Metabolic Studies of High-Dose Busulphan in Adults," *Eur. J. Clin. Pharmacol.,* 36:525–530, 1989.

Lu et al., "Preliminary Results of High-Dose Busulfan and Cyclophosphamide with Syngeneic or Autologous Bone Marrow Rescue," *Cancer Treatment Reports,* 68 (5):711–717, 1984.

Kitamura et al., "Anesthetic Management of Five Patients with Polycythemia Rubra Vera. Importance of Preoperative Managements," *Jpn. J. Anesthesiol.,* 28(5):512–517, 1979. Abstract only.

Miller et al., "A Randomized Trial of Busulfan–Cyclophosphamide (BU–CY) versus Cyclophamide–Total Body Irradiation (CY–TBI) as Preparative Regimen for Patients with Chronic Myelogenous Leukemia (CML)," Blood, 78:1155, 1991. Abstract only.

"Methods of Development of New Anticancer Drugs," *National Cancer Institute Monograph 45,* pp. 147–153, Mar., 1977.

Peters et al., "Clinical and Pharmacologic Effects of High Dose Single Agent Busulfan With Autologous Bone Marrow Support in the Treatment of Solid Tumors," *Cancer Research,* 47:6402–6406, 1987.

Schwertfeger et al., "Early Toxicity of Busulfan/Cyclophosphamide versus TBI/Cyclophosphamide Conditioning for Allogeneic Bone Marrow Transplantation in Patients with Chronic Myelogenous Leukemia," *Blood,* 80(10) (Suppl. 1):2125, 1992. Abstract only.

Sharkis and Santos, "Bone Marrow Transplantation in a BN Rat Model of Acute Myelogenous Leukemia (AML)," *Leukemia Research, :251–252, 1977.*

Sheridan et al., "High-Dose Chemotherapy with Busulphan and Cyclophosphamide and Bone-Marrow Transplantation for Drug-Sensitive Malignancies in Adults: A Preliminary Report," *The Medical Journal of Australia,* 151:379–385, 1989.

Tutschka and Santos, "Bone Marrow Transplantation in the Busulfan-Treated Rat," *Transplantation,* 20(2):101–106, 1975.

Vassal et al., "Dose-Dependent Neurotoxicity of High--Dose Busulfan in Children: A Clinical and Pharmacological Study," *Cancer Research,* 50:6203–6207, 1990.

Vassal et al., "Pharmacokinetics of High-Dose Busulfan in Children," *Cancer Chemotherapy and Pharmacology,* 24:386–390, 1989.

Vaughan et al., "Improved Results of Allogeneic Bone Marrow Transplantation for Advanced Hematologic Malignancy Using Busulfan, Cyclophosphamide and Etoposide as Cytoreductive and Immunosuppressive Therapy," *Bone Marrow Transplantation,* 8:489–495, 1991.

Dialog Search Report printed Mar. 31, 1993.

PARENTERAL BUSULFAN FOR TREATMENT OF MALIGNANT DISEASE

FIELD OF THE INVENTION

The present invention relates to a form of busulfan useful for the suppression of malignancy in humans.

BACKGROUND OF THE INVENTION

Busulfan [1,4-bis-(methanesulfonoxyl)butane], is a bifunctional alkylating agent which was first described by Haddow and Timmis (1953). Since the demonstration of its potent antitumor effects, it has been used extensively for treatment of malignant disease, especially hematologic malignancies and myeloproliferative syndromes (Galton, 1953; Ambs et al., 1971; Abe, 1975; Canellos, 1985; Hughes and Goldman, 1991; Collis, 1980). Its use was for long time limited to low dose oral therapy with palliative intent and frequent monitoring of the blood counts was routinely recommended (Canellos, 1985; Hughes and Goldman, 1991; Collis, 1980). The advent of some 2 to 3% of the patients developing busulfan-induced pulmonary fibrosis (Collis, 1980; Koch and Lesch, 1976; Oakhill et al., 1981), as well as occasionally severe, sometimes even irreversible myelosuppression after prolonged administration effectively deterred dose escalation beyond 8-10 mg daily (Canellos, 1985; Hughes and Goldman, 1991; Ganda and Mangalik, 1973; Albrecht et al., 1971).

In 1974, however, Santos and Tutschka investigated the use of busulfan to create a murine model of aplastic leukemia (Santos and Tutschka, 1974; Tutschka and Santos, 1975). Subsequently, the experience gained in this model system was used to introduce high-dose combination chemotherapy based on oral busulfan for pretransplant-conditioning of primates (Buckner, 1975), and subsequently patients undergoing both autologous and allogeneic marrow transplantation (Santos et al., 1983; Lu et al., 1984; Yeager et al., 1986; Tutschka et al., 1987; Peter et al., 1987; Copelan et al., 1989; Geller et al., 1989; Grochow et al., 1989; Sheridan et al., 1989). Since then, high dose busulfan, most commonly in combination with cyclophosphamide, has proven to be a most effective antileukemic regimen when used in conjunction with autologous or allogeneic hematopoietic stem cell support. A recent comparison between busulfan/cyclophosphamide (BuCy) and cyclophosphamide (Cy) combined with total body irradiation (TBI) for preparation of patients with hematologic malignancies undergoing allogeneic marrow transplantation illustrated that the BuCy regimen was well tolerated and at least as effective as the TBI-based regimen (Miller et al., 1991; Buckner et al., 1992; Schwertfeger et al.; 1992).

High-dose busulfan therapy has several advantages for use in marrow ablation/pretransplant treatment. First, when using chemotherapy alone for conditioning of patients undergoing marrow transplantation, one avoids the dependence on a radiation unit with, usually, limited capacity to deliver the necessary treatment on a fixed schedule. Second, high total radiation doses are very toxic, especially to the lungs, and may require special protective measures (shielding). Such excessive toxicity is usually not seen with combination chemotherapy. Third, a radiation based regimen can only be delivered to patients who have not been previously irradiated. Many patients with lymphoma, Hodgkin's disease and leukemia have had previous (extensive) radiation for control of locally aggressive disease in sanctuary sites like the central nervous system or to sites of bulky disease such as the mediastinum or the neck. Additional radiation as part of the pretransplantation conditioning regimen may cause irreversible and often fatal toxicity in such cases. However, a majority of previously radiated patients can safely receive a busulfan-based regimen, provided that the previous acute radiation toxicity (usually within the first 2-4 months after therapy) has subsided. Fourth, in selected patients who suffer recurrent leukemia after allogeneic marrow grafting, a second marrow transplant may still offer a chance for long-term disease control or even cure (Vaughn et al., 1991; Champlin et al., 1985; Sanders et al., 1988; Blume et al., 1987). Due to subclinical (irreversible) toxicity, a TBI-based regimen can only be utilized once in a patient's life time, whereas combination chemotherapy can be employed following a previous TBI-regimen. Busulfan-based chemotherapy will, therefore, serve as a valid alternative.

Oral busulfan has, unfortunately, several serious shortcomings. Thus, when used in high dose combinations with cyclophosphamide (and possibly additional chemotherapeutic agents), serious side effects in the liver and lungs are often encountered (Collis, 1980; Koch et al., 1976; Santos et al., 1983). Thus, several investigators have reported veno-occlusive disease (VOD) of the liver, leading to fatal liver failure, as the most serious side effect (Yeager et al., 1986; Geller et al. 1989; Grochow et al., 1989; Miller et al., 1991). Neurological disturbances like grand mal seizures and severe nausea and vomiting are also frequently encountered (Grigg et al., 1989; Marcus et al., 1984; Martell et al., 1987; Sureda et al., 1989; Vassal et al., 1990). It is impossible to predict which patients will develop liver failure, and it is further unknown whether the liver failure is due to toxicity from the systemic busulfan or whether it is mainly due to a first-pass phenomenon when busulfan is absorbed from the intestinal tract. Based on the somewhat sketchy information that is available on busulfan pharmacokinetics, it appears however, that patients who absorb a large fraction of the ingested dose, with a prolonged high busulfan plasma concentration, will be at increased risk for developing serious side effects (Marcus et al. 1984; Vassal et al., 1990). Another disadvantage with oral busulfan is, that patients who develop severe nausea and vomiting shortly (within 1-2 hours) after a dose has been delivered, will lose part of or the entire dose, and it may be virtually impossible to accurately determine how much of the dose has been lost in a vomiting subject. Further, the intestinal resorption of any delivered drug may be influenced by the patient's nutritional state, and by concurrent administration of other drugs affecting the intestinal microenvironment, as well as by whether the patient has eaten in close proximity to ingestion of the administered drug dose and, finally, by the inherent biological variability in intestinal absorption between different patients (Benet et al., 1985). Due to these uncertainties, oral administration of high-dose busulfan carries with it an inherent safety problem both from the potential danger of inadvertent overdosing with a risk for (lethal) toxicities, as well as from the hazard of (suboptimal) underdosing the patient with an inadvertently high potential for recurrent or persistent malignancy after the marrow transplant.

The in vivo distribution of busulfan labeled with the positron-emitting radionuclide carbon 11 was investigated in cynomolgus monkeys and in a human patient using positron emission tomography (Hassan et al., 1992). Radiotracer amounts of 11C-busulfan in a saline solution containing 10% ethanol were injected as an i.v. bolus. The concentration of busulfan was not reported but was likely insignificant compared to therapeutic levels. M Hassan has indicated to the inventor that the total dose injected was estimated at 1-2 μg.

Giles et al. (1984) reportedly used busulfan to induce platelet dysfunction in rabbits by an intraperitoneal injection of busulfan dissolved in polyethyleneglycol at a dose of 60 mg/kg. The concentration of the solution is not given, and due to the slow solubilization of the busulfan, the authors heated the mixture excessively to promote mixing. This may have caused significant chemical degradation of the busulfan. Furthermore, busulfan given intraperitoneally is very toxic and causes significant local tissue damage.

An abstract of Kitamura's article (Kitamura, et al., 1979) relates to the well-known use of busulfan and cyclophosphamide which are typically given orally. The $^{32}$P is reported to have been administered intravenously.

In a study of bone marrow transplantation in the busulfan-treated rat, Tutschka and Santos reportedly injected busulfan prepared in 2.5% carboxymethylcellulose in water i.p. This injection also causes significant local tissue damage.

To circumvent the above shortcomings and hazards from oral administration of busulfan for chemotherapy with myeloablative intent, a chemically stable busulfan formulation that can be safely administered parenterally, i.e., via the intravenous (i.v.) route is needed.

ABBREVIATIONS

AUC=Area under the curve
BSF=Busulfan
BuCy=Busulfan/cyclophosphamide
CGA=N-(2,6-difluorobenzoyl)-N-[3,5-dichloro-4-(3-chloro-5-trifluoromethylpyridin-2-yloxy)-phenyl]urea
Cy=Cyclophosphamide
DDCB=1,4-Bis(diethyldithiocarbamoyl)butane
DDTC=Sodium diethyldithiocarbamate
DMA=N', N-dimethylacetamide
DMSO=Dimethylsulfoxide
HBCD=hydroxypropylbetacyclodextrin
MTT=3,(4,5-dimethylthiazol-2-yl)2,5-diphenyltetrazolium-bromide
PEG=Polyethyleneglycol
PG=Propyleneglycol
TBI=Total body irradiation
THF=Tetrahydrofuran
TVP=Total volume percent

SUMMARY OF THE INVENTION

The present invention involves methodology for dissolving busulfan in a liquid vehicle(s) to provide a physiologically acceptable busulfan formulation for parenteral administration, such that the busulfan remains chemically stable and can be administered without unexpected toxicity from undissolved busulfan or from the liquid vehicle when the formulation is administered parenterally to the recipient at maximally tolerated busulfan doses.

In a broader sense, the present invention describes a method of administering busulfan parenterally as to avoid the erratic intestinal absorption that is experienced after oral administration of this agent, thereby circumventing the unpredictable and sometimes lethal toxicity.

The present invention provides a method for treating malignant disease in an individual. The method comprises the parenteral administration of a pharmaceutically effective amount of busulfan dissolved in a water miscible, physiologically acceptable busulfan solvent. The mixture of dissolved busulfan and solvent may further include water. Malignant disease may be a tumor, a hematologic malignancy, a myeloproliferative syndrome, leukemia, or a disease requiring bone marrow transplantation, for example. A pharmaceutically effective amount of dissolved busulfan is an amount that achieves a therapeutic goal. A physiologically acceptable solvent is a solvent which is tolerated by the individual in the concentrations and doses used. The water miscible, physiologically acceptable busulfan solvent is a solvent that dissolves busulfan and may be N', N-dimethylacetamide, an aqueous solution of polyethyleneglycol or a mixture of N'N-dimethylacetamide and an aqueous carrier solution allowing busulfan solubility and stability. The aqueous carrier solution may be a polyethylene glycol solution. The administration may be intravascular or intravenous. The concentration of N', N-dimethylacetamide is 5%-99%, preferably 5%-15% or 15%-25%, and the concentration of polyethyleneglycol is 5%-50%. The polyethyleneglycol may have a molecular weight between 200 and 2,000 daltons, more preferably between 350 and 450 daltons. One skilled in the art would realize that polyethyleneglycol solutions of various molecular weights could be used as long as they are physiologically acceptable. The dissolved busulfan may have a concentration of 1-75 mg/ml.

A further embodiment of the present invention is a pharmaceutically acceptable formulation for parenteral administration of busulfan. The formulation comprises busulfan dissolved in a water miscible, physiologically acceptable busulfan solvent at a concentration of 1-75 mg/ml. The formulation may further comprise water. The water miscible busulfan solvent may be N',N-dimethylacetamide, an aqueous solution of polyethyleneglycol or a mixture of N'N-dimethylacetamide and an aqueous carrier solution allowing busulfan solubility and stability. The aqueous carrier solution may be a polyethylene glycol solution. The N'N-dimethylacetamide is at a concentration of 5%-99% and the polyethyleneglycol is at a concentration of 5%-50%. The polyethyleneglycol may have a molecular weight between 200 and 2,000 daltons, more preferably between 350 and 450 daltons. The busulfan solvent may be propylene glycol or an aqueous solution of hydroxypropylbetacyclodextrin.

The present invention provides for further pharmaceutically acceptable formulations for parenteral administration of busulfan, for example, formulations comprising 1-7.5 mg/ml dissolved busulfan, 35%-45% polyethyleneglycol, 45%-55% water, and 5%-15% N'N-dimethylacetamide. A preferred embodiment is a pharmaceutically acceptable formulation for parenteral administration of busulfan comprising 1-15 mg/ml dissolved busulfan, 35-45% polyethyleneglycol-400, 35-45% water and 15-25% N'N-dimethylacetamide A method of preparing a pharmaceutically acceptable formulation for parenteral administration of busulfan is an aspect of the present invention. The method comprises the steps of i) dissolving busulfan in a water miscible, physiologically acceptable busulfan solvent to yield a working solution of busulfan; and ii) diluting the busulfan working solution with an aqueous carrier solution allowing busulfan solubility and stability to yield a pharmaceutically acceptable formulation for parenteral administration of busulfan. A further method comprises the step of dissolving busulfan at a concentration of 1-75 mg/ml in a water miscible, physiologically acceptable busulfan solvent. The solvent may be N'N-dimethylacetamide or an aqueous solution of polyethyleneglycol.

DETAILED DESCRIPTION OF THE PREFERRED EMBODIMENTS

Figure 1A:
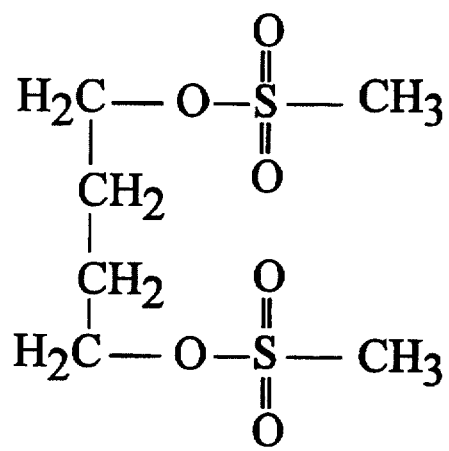
FIGS. 1A-1C schematically show the chemical structure of busulfan as free drug (FIG. 1A) and derivatized with diethyldithiocarbamate sodium (FIG. 1B) to yield 1,4-bis(diethyldithiocarbamoyl) butane (DDCB) (FIG. 1C) after extraction for HPLC analysis.

This invention provides methods and compositions useful for parenteral administration of particular formulations of busulfan to assist in the control of malignant disease. This route of administration has not been previously explored in the clinical practice of oncology.

The parenteral administration of this chemotherapeutic agent makes it possible to avoid the erratic intestinal absorption that makes oral administration of high dose busulfan suboptimal. The present examples show that the diluent vehicles used in the parenteral preparation of busulfan are effective to dissolve the drug in a chemically stable fashion, such that the drug retains its cytotoxic properties. The vehicles are acceptable to laboratory animals and humans in the proposed concentrations and total doses to be used; PEG-400 has been previously evaluated clinically for use as a carrier of L-asparaginase in the treatment of lymphocytic leukemia and lymphoma, and no unexpected or adverse toxicity attributable to the use of this vehicle was experienced (Keating et al., 1993). Other PEG sizes which are pharmaceutically acceptable may be likewise used. DMA has previously been used as a stock diluent for Amsacrine when used in clinical studies of treatment for acute myeloid leukemia, where no serious adverse effects attributable to the DMA have been documented. DMA has been used in phase I studies as an anticancer agent in man (Weiss et al., 1962). The dose-limiting toxicities were hepatic dysfunction, hypotension and mental excitatory states in patients treated with doses of at least 400 mg/kg body weight daily for 4-5 days or cumulative doses exceeding 88 g, but all the toxicity was reversible on the cessation of treatment (Weiss et al., 1962). As an alternative solvent, propylene glycol has been cited as harmless when taken internally, probably because its oxidation yields pyruvic and acetic acids (Merck Index, 11th Ed., 1989).

The data presented herein from a murine model indicate that the parenteral busulfan preparation provides a substantially higher bioavailability than any of the oral preparations tested. Specifically, the DMA/aqueous PEG-400/busulfan solution is chemically stable, easy to prepare and handle at room temperature, and provides reliable and easily controllable dosing with 100% bioavailability. For comparison, while busulfan can be dissolved at 25 mg/ml in acetone, this solvent is highly hemolytic and unacceptable for use as a clinical solvent in humans. Alternatively, e.g., DMSO could be considered as an effective solvent of busulfan. DMSO is, however, a chemically highly reactive reagent, which rapidly degrades busulfan, making it an unsuitable solvent for clinical routine use. In an experimental situation, both acetone and DMSO can be utilized as solvents for busulfan, and pharmacokinetic data were obtained with these vehicles for comparison to busulfan dissolved in the DMA/PEG-400 aqueous solvent system. Oral busulfan administration gives a wide range of resulting plasma concentrations which influence the resulting toxicity profile, especially when the drug is used in supralethal doses as part of pretransplant conditioning regimens. The clinical experience with busulfan underlines the general problem of giving optimal therapy when using the oral route of administration for a chemotherapeutic agent.

The present invention provides high-dose parenteral busulfan therapy for the treatment of malignant disease, while substantially circumventing the inherent problems of erratic intestinal absorption, first-pass effects, toxicity, and liver metabolism of the administered agent. The present invention provides the opportunity to design and execute pharmacologic and therapeutic studies of high-dose busulfan-based therapy for malignant disease with hematopoietic stem cell support in an optimally controlled fashion, such that for the first time a valid comparison can be performed between a busulfan-based and other chemotherapy- vs. TBI-based conditioning regimens. Furthermore, the chemically stable busulfan preparation can be used for regional therapy such as isolated limb perfusion, and local treatment of malignant effusions in the pleural space and peritoneal cavity. There is a severe shortage of chemotherapeutic drugs that can be successfully used in the local treatment of malignant effusions.

Malignant cells may be eradicated from the body by administering busulfan-based chemotherapy in high doses. The present invention of a parenteral preparation of busulfan represents a new and more effective tool for administering precise doses of such therapy while diminishing the risk of suffering life-threatening or lethal adverse effects as a result of the administered treatment.

Unless defined otherwise, all technical and scientific terms used herein have the same meaning as commonly understood by one of ordinary skill in the art to which this invention belongs. All percentages are weight-/volume percentages unless otherwise noted.

EXAMPLE 1

A Formulation of Busulfan Acceptable for Parenteral Administration

The present example provides formulations of prototype parenteral preparations of busulfan with estimates of different degrees of solubility determined with a newly developed high pressure liquid chromatography (HPLC) assay for busulfan.

METHODOLOGY:

Calculation of Desired Target Solubility.

Busulfan has a solubility of only 25 μg/ml in water at room temperature. The currently used high-dose busulfan regimens prescribe an estimated daily dose of 280 mg for a 70-kg subject (1 mg/kg body weight every 6 hours) (Santos et al., 1983; Yeager et al., 1986). With a clinically safe maximum infusion rate of about 4–5 ml/min over 120 minutes, the busulfan should be dissolved at a concentration of at least 2–4 mg/ml. This requires at least an 80 fold increase in solubility over the aforementioned.

Approaches to Enhance Busulfan Solubility in Aqueous Solution.

Polyethyleneglycol-(PEG) 400 —aqueous solvent system; solvents of combinations of PEG-400, propyleneglycol (PG) and glycerin; N'N-dimethylacetamide and combinations of N',N-dimethylacetamide with 40% PEG-400 in aqueous solution were examined. A cyclodextran aqueous medium was tested. For limited comparative pharmacokinetic studies in the murine model, busulfan was also dissolved in pure acetone and in DMSO at 3 mg/ml immediately prior to intravenous administration. The detailed vehicle system compositions are shown in Table 1.

TABLE 1

| Solvent Systems for Parenteral Formulation of Busulfan | | | | | | | | | | |
|---|---|---|---|---|---|---|---|---|---|---|
| Ingredient | Formulation Number | | | | | | | | | |
| (%, w/v) | 1 | 2 | 3 | 4 | 5 | 6 | 7 | 8 | 9 | 10 |
| PEG-400 | 30 | 10 | 40 | 10 | 0 | 40 | 40 | 0 | 0 | 0 |
| PG | 10 | 10 | 0 | 10 | 0 | 0 | 0 | 0 | 0 | 0 |
| Glycerin | 10 | 30 | 0 | 10 | 0 | 0 | 0 | 0 | 0 | 0 |
| Cyclodextran | 0 | 0 | 0 | 0 | 7 | 0 | 0 | 0 | 0 | 0 |
| Water | 50 | 50 | 60 | 70 | 93 | 40 | 50 | 0 | 0 | 0 |
| DMA | 0 | 0 | 0 | 0 | 0 | 20 | 10 | 0 | 0 | 100 |
| Acetone | 0 | 0 | 0 | 0 | 0 | 0 | 0 | 100 | 0 | 0 |
| DMSO | 0 | 0 | 0 | 0 | 0 | 0 | 0 | 0 | 100 | 0 |

A known amount of busulfan was equilibrated in the solvent system at 20°C. for predetermined periods of time. An aliquot was then removed and subjected to HPLC assay after an appropriate dilution for determining busulfan concentration and stability.

HPLC Assay.

The most sensitive detection system for busulfan in the HPLC assay would utilize an absorbance or fluorescence detector operating in the ultraviolet (UV) spectrum. However, the busulfan molecule has no UV absorbing chromophore in its structure, and therefore, derivatization with a chromophore is mandatory to facilitate the use of a UV detector in the HPLC assay.

Derivatization.

Figure 1B:
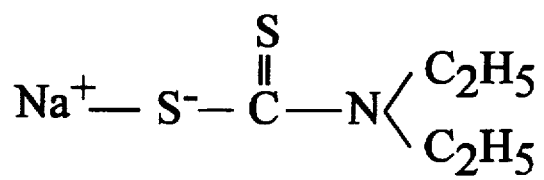
Figure 1C:
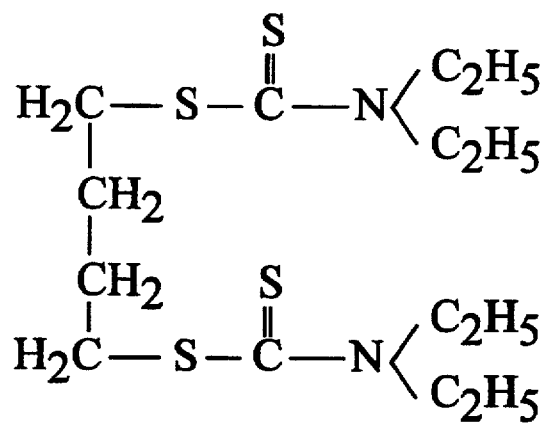

A modification of the procedure of MacKicham and Bechtel was employed (MacKicham et al., 1990). Briefly, diethyldithiocarbamate sodium was used as the derivatizing agent to yield 1,4-bis(diethyldithiocarbamoyl) butane (FIG. 1) with peaks of absorbance at 278 and 254 nm.

Conditions for the HPLC Assay.

The derivatized product was separated from the reaction mixture using Sep-Pak ™ $C$18 solid phase extraction vials (Waters Chromatography Systems Inc., Millford, Mass.). Two HPLC systems were evaluated. The different mobile phase systems are shown in Table 2.

TABLE 2

| | HPLC Conditions | |
|---|---|---|
| | Assay-1 | Assay-2 |
| Column | C18 | C18 |
| Mobile phase | Acetonitrile:Water:THF (55:25:20 v/v, pH 4.2) | Methanol:Water (81:19 v/v) |
| Flow rate | 0.8–1.0 ml/min | 1.0 ml/min |
| UV Absorb. | 254 (and 278) nm | 254 and 278 nm |
| Chart speed | 20 cm/hr | 10 cm/hr |
| Int. std. | (CGA-112913)[b] | urea, 500 μg/ml |
| Ret. time: | | |
| DDCB | 7.5 min | 8.4 min |
| Int. std. | 8.7–9.0 min | 10.2 min |

[b]CGA-112913; N-(2,6,-difluorobenzoyl) -N-[3,5,-dichloro-4-(3-chloro-5-trifluoromethylpyridin-2-yloxy)phenyl] urea, was a gift from CIBA-Geigy, Inc. (Basel, Switzerland). It was identified as a suitable internal standard for assay-1 after the initial stability studies had been performed utilizing assay-2.

RESULTS

Solubility Determinations.

The solubility of busulfan in the respective individual solvent systems are displayed in Table 3.

TABLE 3

| Solubility of Busulfan in Various Solvent Systems | |
|---|---|
| Formulation | Solubility (mg/ml) |
| 1 | 1.66 |
| 2 | 3.32 |
| 3 | 3.40 |
| 4 | 2.09 |
| 5 | 3.19 |
| 6 | 4.94 |
| 7 | 2.6 |
| 8 | 3.0 |
| 9 | 3.0 |
| 10 | 75.0 |

The solubility of busulfan significantly increased in all nine systems tested; ranging from 66 to 197 fold compared to the solubility in water. Therefore, the formulation of a parenteral form of busulfan at 2–4 mg/ml is feasible. At this solubility, a longer than 120 minute infusion duration should not be needed to achieve a clinically prescribed dose of 1 mg/kg body weight in heavy subjects.

EXAMPLE 2

Equilibrium Solubility and Stability Studies of Parenteral Preparations of Busulfan The present example provides a design of a chemically stable formulation of busulfan that is suitable for parenteral administration, studies of limits of solubility when accordingly formulated busulfan is mixed with infusion fluids such as saline and dextrose, studies of chemical and physical stability of busulfan in the proposed parenteral preparation during the infusion period, toxicity of the solvent system in terms of hemolysis potential, and in vitro cytotoxic activity of vehicle(s) with and without the addition of busulfan.

METHODOLOGY:

Equilibrium Solubility Studies.

PEG-400 aqueous solutions of 40 and 50% (v/v), and hydroxypropylbetacyclodextrin (HBCD) aqueous solutions of 10, 25, and 45% (w/w) were prepared by mixing with distilled water at room temperature (22° C.). An excess amount of busulfan was added to each solution and the mixtures were placed on a rotating mixer (Tube Rotator TM, Scientific Equipment Products, Baltimore, Md.). Samples of 1 ml were taken at various time intervals, filtered through a 0.45 μm filter (Acro LC 25 filter TM Millipore Corp. Bedford, Mass.), on a syringe filtration assembly (Nuclepore Corp. Pleasanton, Calif.), and after appropriate dilution and derivatization with sodium diethyldithiocarbamate, the busulfan concentration was determined by HPLC as described in Example 1. For the DMA/PEG-400 aqueous vehicle, a slightly modified approach had to be taken, since DMA readily dissolved the ACRO LC 25 filter. After dissolving the busulfan in DMA, the busulfan-DMA solution was mixed with 40% PEG-400/40% water and filtered through a 0.45 μm silver filter (Nuclepore Corp., Pleasanton, Calif.) fitted to a syringe assembly. After derivatization with DDTC, the busulfan concentration was determined by HPLC as above.

Osmotic Pressure Measurement.

Osmotic pressure measurements were carried out on an Advanced Digimatic Osmometer TM (Model 3D II, Advanced Instruments Inc., Needham Heights, Mass.). The instrument was calibrated using Osmet TM calibration standards (Precision Systems 5004, Curtin Matheson Scientific, Houston, Tex.) over a range of 100-2000 mOsm/kg. The test solution was placed in a disposable cuvette in a volume of 250 μl, and the osmotic pressure reading was recorded after equilibration in units of mOsm/kg. Triplicate measurements were carried out for each tested vehicle solution (without busulfan) and six measurements were done with busulfan added.

Stability of the Various Busulfan Formulations. The physical and chemical stabilities of the various parenteral busulfan formulations were examined as follows: First, busulfan was dissolved at a concentration of 25 mg/ml in DMA only ("stock solution") and incubated at 4° C. at 22° C. and at 40°C. Starting at time zero, then weekly up to 10 weeks, samples were withdrawn and analyzed for busulfan concentration by HPLC. Second, the busulfan-DMA was diluted with PEG-400/water to give final concentrations of DMA:PEG-400:water of 20:40:40 and final busulfan concentrations of 2-10 mg/ml. These formulations were subsequently analyzed by HPLC immediately after mixing and then hourly for eight hours. Third, busulfan formulation mixtures were diluted in normal saline to a final busulfan concentration of 1 mg/ml. The preparations were then introduced into infusion bags (Viaflex TM Baxter Healthcare Corp Deerfield, Id.), and allowed to run through a parenteral infusion set at a rate of 1 ml/min. Samples were collected at 0, 0.5, 1.0, 2.0, 5.0, 7.0, 9.0, and 12 hours and analyzed for busulfan by HPLC as above.

Hemolysis Studies.

The procedure of Reed and Yalkowsky was employed for the studies of hemolytic potential of the different preparations, and the LD50 values of the various formulations were evaluated (Reed et al., 1985).

Variable amounts of whole blood (citrated) were added to 0.05 ml of the drug formulations in ratios of 1:1 (v/v), 1:3, 1:5, 1:7, and 1:9. The mixtures were vortexed for 10 seconds and then incubated for 2 minutes at 25°C. Five ml normal saline was then added to this blend to quench further lysis of the erythrocytes by rendering the preparation nearly isotonic. The mixture was again vortexed for 10 seconds and centrifuged for 5 minutes at 3,000 r.p.m. (Beckman Model TJ-6 Centrifuge, Beckman Instruments Inc., Palo Alto, Calif.). The supernatant was carefully aspirated and discarded. The packed erythrocytes were washed once more at room temperature with one volume of normal saline. After centrifugation, the supernatant was again carefully aspirated and discarded. Subsequently, 1 ml of water was added for every 0.1 ml of erythrocytes used. After vortexing for 10 seconds, the mixtures were centrifuged for 5 minutes at 3,000 r.p.m. The absorbance of the supernatant was subsequently measured at 540 nm after a 1:3 dilution with distilled water° Normal saline was assayed in parallel as a standard. The fraction of healthy erythrocytes was defined as the absorbance reading of the respective drug formulation divided by that of the saline standards (Reed et al., 1985).

Statistical Analysis.

The osmotic pressure measurements were subjected to a two-tailed t-test to evaluate the difference between the various vehicle formulations with and without the addition of busulfan. The difference between the means of the two groups was considered significantly different for P less than or equal to 0.05 (Mann et al., 1947).

In vitro Cytotoxicity of Busulfan in the DMA/PEG-400 Vehicle. Human leukemic KBM-3 cells (Anderson, et al., 1992), were incubated for 24 hours in the complete vehicle without the addition of busulfan at different concentrations (0.5%, 1.0%, 2.0%, 3.0% and 100%, v/v), to assay the cytotoxic properties of the 20% DMA/40% PEG-400 aqueous vehicle by itself (negative controls), or with the addition of busulfan. In parallel, cells in Iscove's modified Dulbecco medium (GIBCO, Grand Island, New York, N.Y.), supplemented with 10% fetal bovine serum, were incubated with busulfan (at 25 μg/ml and 50 μg/ml), in the 20% DMA/40% PEG-400 aqueous solvent (the resulting vehicle concentrations were 1.0 and 2.0% (v/v), respectively), or with busulfan dissolved in a small volume (≦1%, v/v) of acetone (positive controls). After 24 hours, 25 μl of a 5 mg/ml solution of MTT (3, [4,5-dimethylthiazol-2-yl]2,5-diphenyltetrazoliumbromide, obtained from Sigma Chemicals, St. Louis, MO), was added to each sample, and after an additional 2 hours of incubation at 37° C., 100 μl of extraction buffer was added (extraction buffer: 20% (w/v) SDS dissolved to saturation at 37° C. in a solution of equal parts of dimethylformamide and deionized water; the pH was adjusted to 4.7 by the use of acetic acid and 1 N HCL as described (Hansen et al., 1989). After over night incubation at 37° C., the optical densities at 570 nm were measured using a Titer-Tech 96-well multi-scanner, using the extraction buffer as the blank. The cytotoxicity was determined as the difference between the samples as above and the reactivity of cells incubated in PBS alone. All determinations were performed in triplicate.

RESULTS

Equilibrium Solubility Determinations.

Maximum solubility of busulfan in the HBCD formulations was reached relatively rapidly with equilibrium attained within one hour at all concentrations of HBCD. An approximate equilibrium solubility of busulfan of 5.6 mg/ml was achieved in the 45% HBCD formulation, with 4.6 and 3.2 mg busulfan per ml in the 25%, and 10% HBCD formulations respectively (Table 4).

TABLE 4

Busulfan Equilibrium Solubility in Various Solvent Systems

| Formulation[a] | Solubility (mg/ml) |
|---|---|
| 10% HBCD (w/v) | 3.18 |
| 25% HBCD (w/v) | 4.57 |
| 45% HBCD (w/v) | 5.56 |
| 40% PEG-400 (v/v) | 3.01 |
| 50% PEG-400 (v/v) | 6.18 |
| 20% DMA / 40% PEG-400 (v/v) | >3.00 |

[a]All formulations were made up to 100% in water

Figure 2:
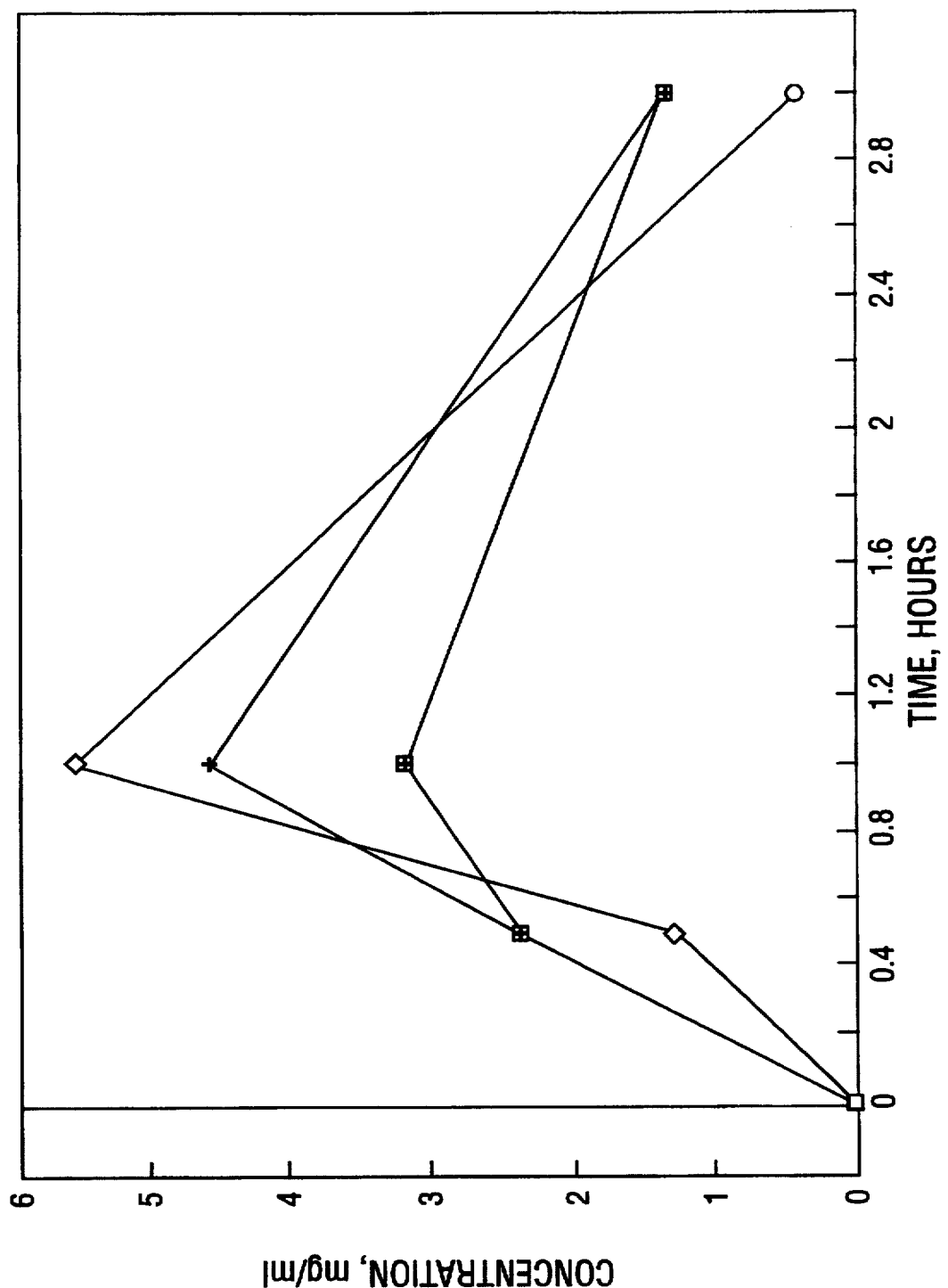
FIG. 2 shows busulfan equilibrium solubility with time in various concentrations of HBCD formulations (□=10%-HBCD; +=25%-HBCD; ◇=45%-HBCD).
Figure 3:
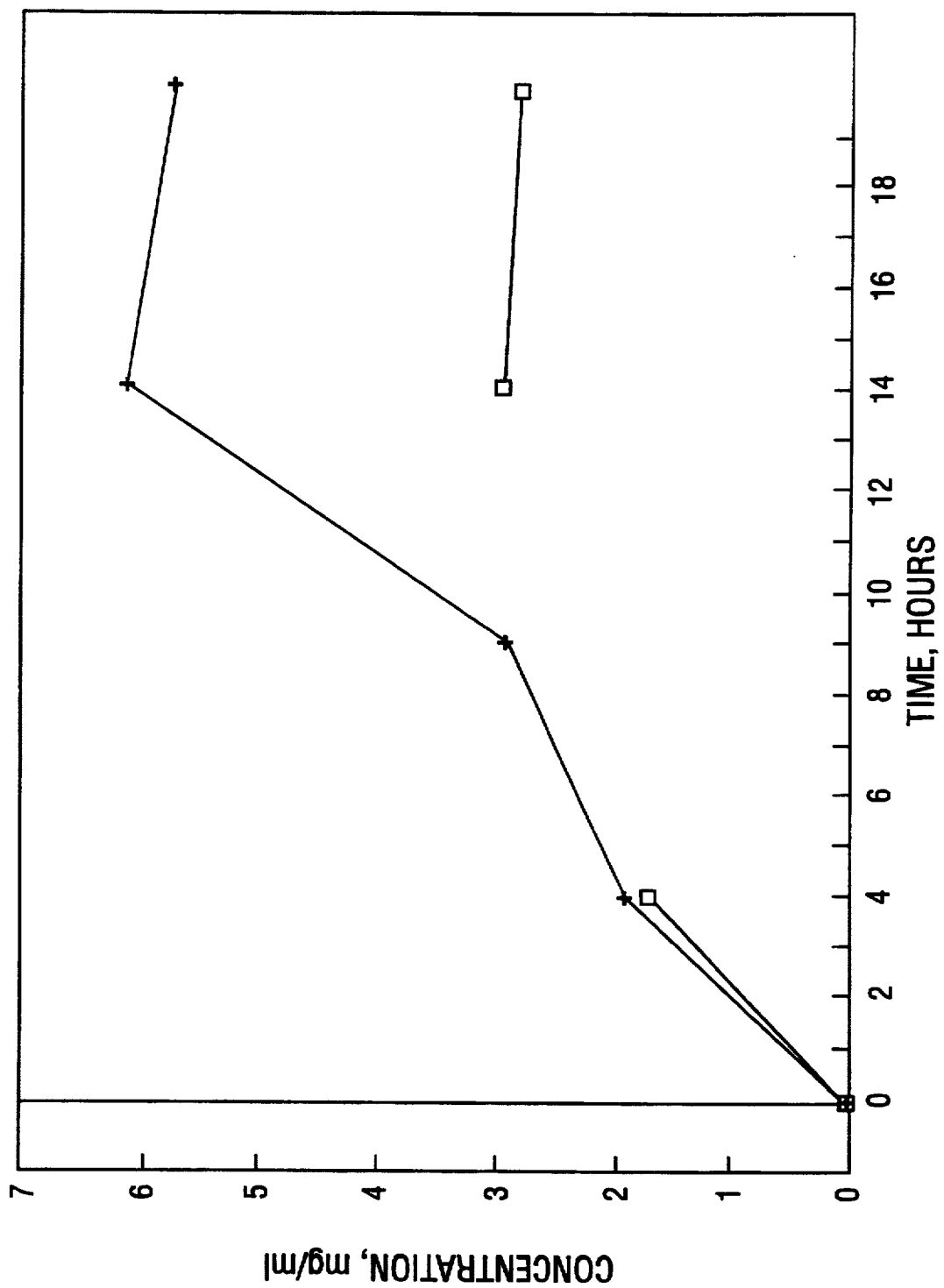
FIG. 3 shows busulfan equilibrium solubility with time in various concentrations of PEG-400 formulations (□=40% PEG-400; +=50% PEG-400).
Figure 7:
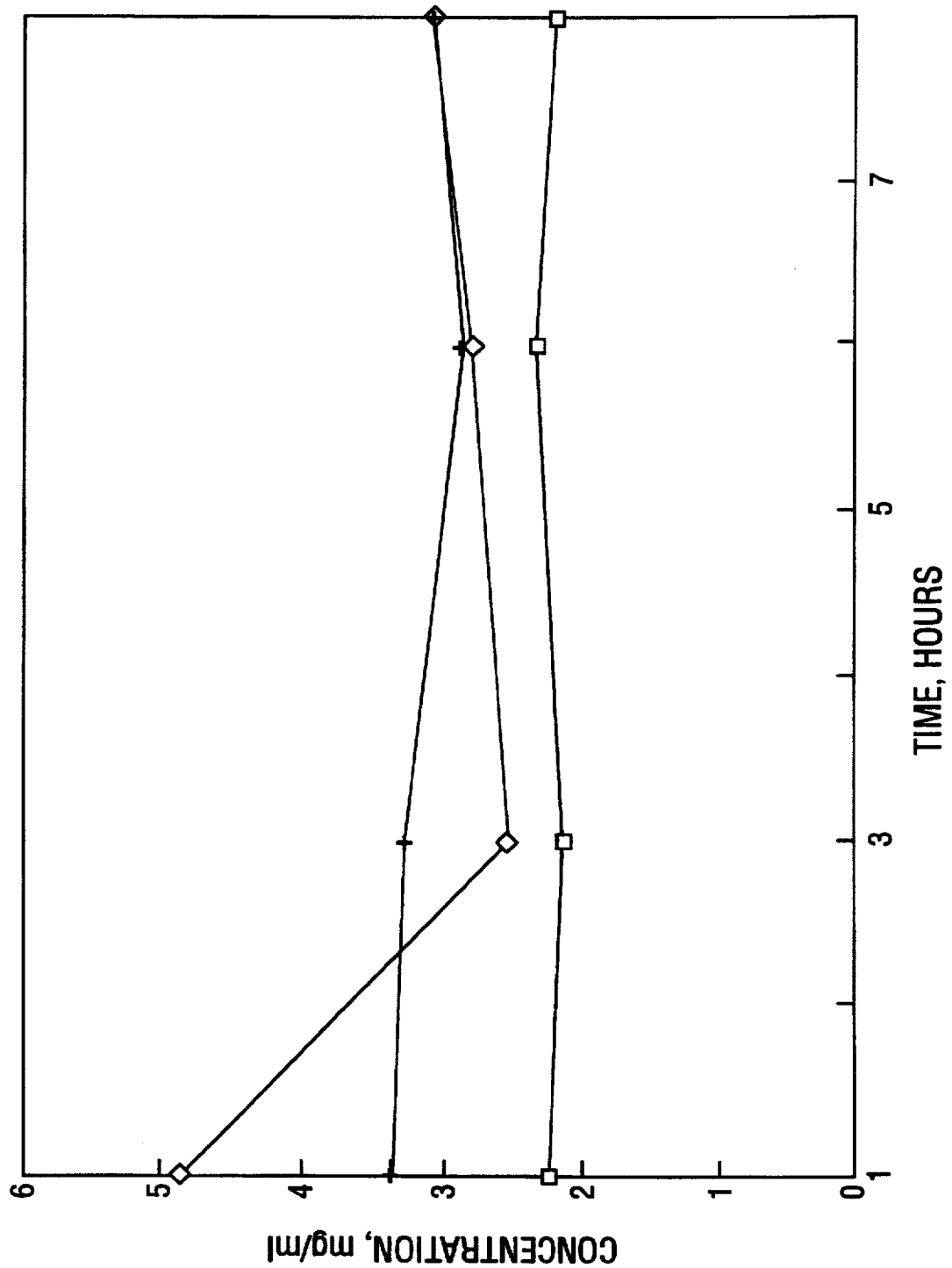
FIG. 7 shows the stability of busulfan at different concentrations in the 20% DMA/40% PEG-400 aqueous vehicle at 22° C. (◇=5 mg/ml; +=3 mg/ml; □=2 mg/ml).

The busulfan concentration in the 25% and 45% HBCD formulations declined rapidly after equilibrium, probably due to chemical degradation of busulfan in this vehicle (FIG. 2). In contrast, in PEG-400 alone, equilibrium solubility was reached slowly; its maximum was not reached for 14 hours (FIG. 3). The 40% and 50% (v/v) PEG-400 formulations yielded maximum busulfan solubility of approximately 3.0 and 6.2 mg/ml respectively (Table 4). Once the maximum solubility was reached, however, the busulfan appeared stable in these vehicles (FIG. 3). To avoid the slow initial solubilization of busulfan in PEG-400, the present inventors introduced an initial step of dissolving busulfan in anhydrous N', N-dimethylacetamide (DMA), followed by mixing it with PEG-400/aqueous solution to final concentrations of 20% DMA/40% PEG-400/40% water. Busulfan may be dissolved in DMA at 75 mg/ml, but was routinely dissolved in a "working" stock solution of 25 mg/ml. This stock solution of busulfan in DMA was stable at 4° C. and at 22° C. for more than 10 weeks without appreciable decay. At 40C. some degradation (approximately 10-20%) was noted, starting gradually from about three weeks and at 15 weeks being in the order of 50%. The composite DMA/PEG400/aqueous solvent provided a maximum transient busulfan solubility of approximately 10 mg/ml. This "complete" busulfan formulation was stable at room temperature for more than 8 hours when the busulfan concentration was ≦3 mg/ml. At higher concentrations (5-10 mg/ml), the drug started precipitating after one hour. This precipitation continued until a new apparent equilibrium solubility of about 3 mg/ml had been established (see FIG. 7).

Osmotic Pressure.

It is desirable to formulate a parenteral administration form that is isosmotic to human blood, but a highly hypertonic delivery system can be utilized if the drug/solvent is infused through a central vein catheter and rapidly diluted by a high blood volume. The osmolarity of the various busulfan formulations are shown in Table 5.

TABLE 5

Osmotic Pressure Measurement[a]

| Number | Formulation | Osmotic Pressure, mOsm/kg | (S.D.) |
|---|---|---|---|
| 1 | Water | 0.00 | |
| 2 | Normal Saline | 233.0 | (5.00) |
| 3 | Blood | 290.7 | (0.47) |
| 4 | 10% HBCD | 82.33 | (1.25) |
| 5 | 10% HBCD-busulfan | 92.67 | (1.97) |
| 6 | 45% HBCD | 298.7 | (9.98) |
| 7 | 45% HBCD-busulfan | 325.5 | (13.30) |
| 8 | 40% PEG-400 | 1661. | (10.00) |
| 9 | 40% PEG-400-busulfan | 1729. | (5.00) |
| 10 | 50% PEG-400 | 2088. | (6.53) |
| 11 | 50% PEG-400-busulfan | 2672. | (15.41) |
| 12 | 20% DMA / 40% PEG-400 | 4653. | (8.50) |
| 13 | 20% DMA / 40% PEG-400-busulfan | 4416. | (6.20) |

[a]the mean from 3-6 independent determinations.

The PEG-400 formulations with and without busulfan were very hypertonic; their osmotic pressures ranged from 1661 to more than 4000 mOsm/kg as compared with the 290 mOsm/kg for blood.

The 10% HBCD solutions with and without busulfan were hypotonic, their osmolarity ranging from 82 to 93 mOsm/kg. The 45% HBCD solution was isosmotic compared with blood. Addition of busulfan increased the osmolarity in all the formulations studied except the 20% DMA/40% PEG aqueous solution (Table 5) (P <0.05).

Physical and Chemical Stabilities of the Formulations.

The physical and chemical stability of busulfan in the various solvent formulations was studied.

The drug was first dissolved in DMA at 25 mg/ml. Different aliquots were stored at 4° C., at 22° C., and at 40°C. From time 0 and then weekly, samples were analyzed for busulfan drug degradation over at least 15 weeks of observation. When stored at 40° C., the samples showed degradation of busulfan starting around 3 weeks and at 15 weeks it amounted to about 50%. The stability of busulfan in the complete 20% DMA/40% PEG-400/40% water was also studied for the following different busulfan concentrations, 2, 3, 5, 8, and 10 mg/ml. At 2 and 3 mg/ml the busulfan was stable for the duration of the 8 hour observation period in this solvent system. At 5, 8, and 10 mg/ml, a precipitate started forming after 1-2 hours and the concentration of free busulfan gradually decreased to about 3 mg/ml, which therefore appears to be the maximum solubility at 22° C. in this vehicle (see FIG. 7).

To examine the drug stability during a prolonged infusion, the busulfan was dissolved at 5 mg/ml in 40% and 50% aqueous PEG-400 and at 4 mg/ml in the 10%-HBCD. The mixtures were then filled into (clinically utilized) infusion fluid transfer bags, (300 ml Viaflex ™ bags, Baxter Healthcare Corp., Deerfield, Ill.). The busulfan was subsequently evacuated through an infusion tubing set (Quest Medical Inc., Dallas, Tex.), at a rate of 1 ml/min, and samples taken for drug analysis at regular time intervals (at 0, 0.5, 1, 2, 5, 7, 9, and 12 hours). After derivatization of the busulfan as described above the samples were analyzed with HPLC. Interestingly, an initial decrease in busulfan concentration, probably from early drug adsorption to the walls of the infusion container and the tubing set was detected. Thereafter, the busulfan concentration remained constant up to at least five hours in the 10% HBCD vehicle, and for at least 7 hours in the different PEG-400 formulations.

Hemolysis.

Figure 4:
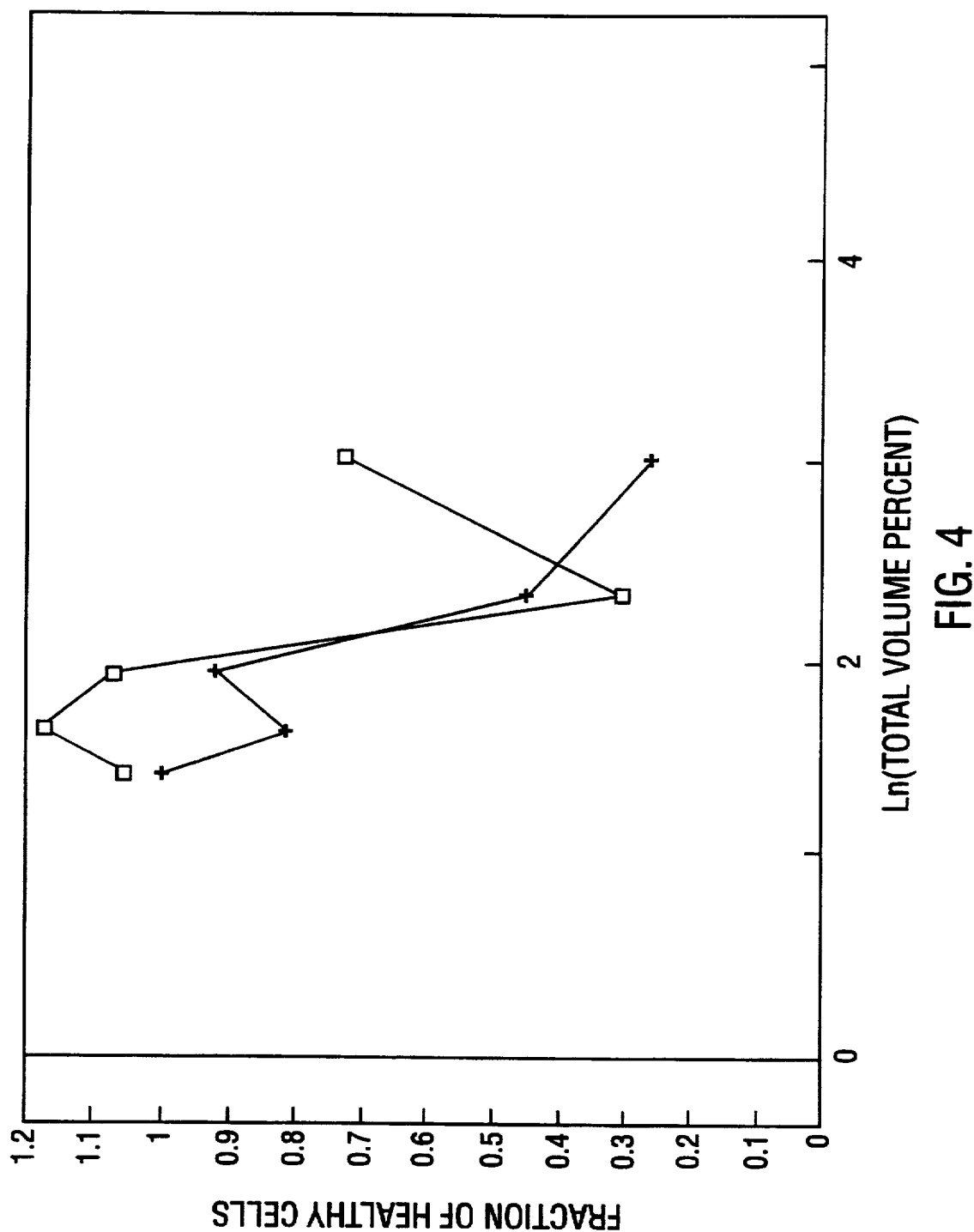
FIG. 4 shows the hemolytic effects of 40% PEG-400 with and without busulfan on human erythrocytes (□=40% PEG-400; +=40% PEG-400-BSF).
Figure 5:
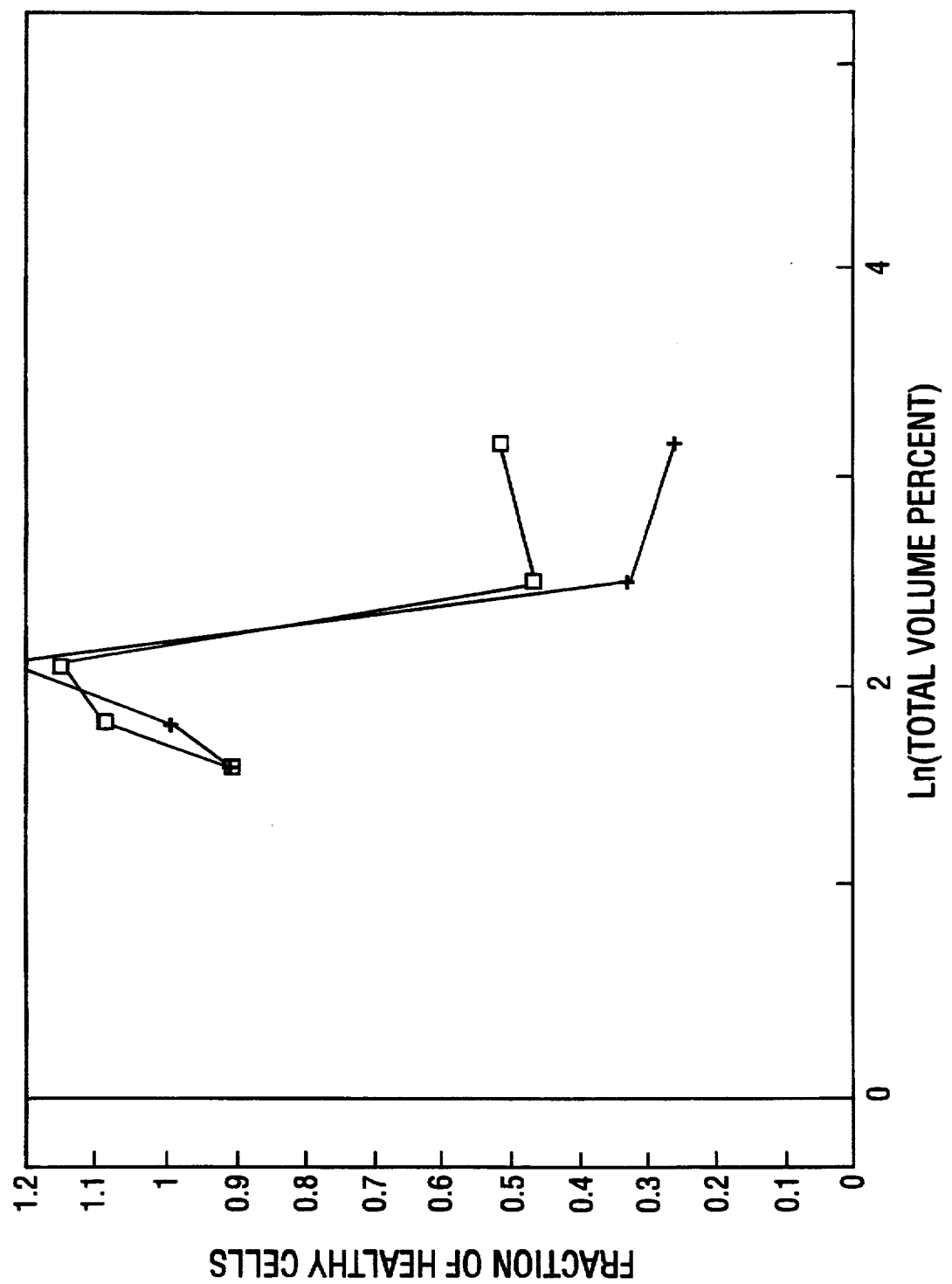
FIG. 5 shows the hemolytic effects of 50% PEG-400 with and without busulfan on human erythrocytes (□=50% PEG-400; +=50% PEG-400 BSF).
Figure 6:
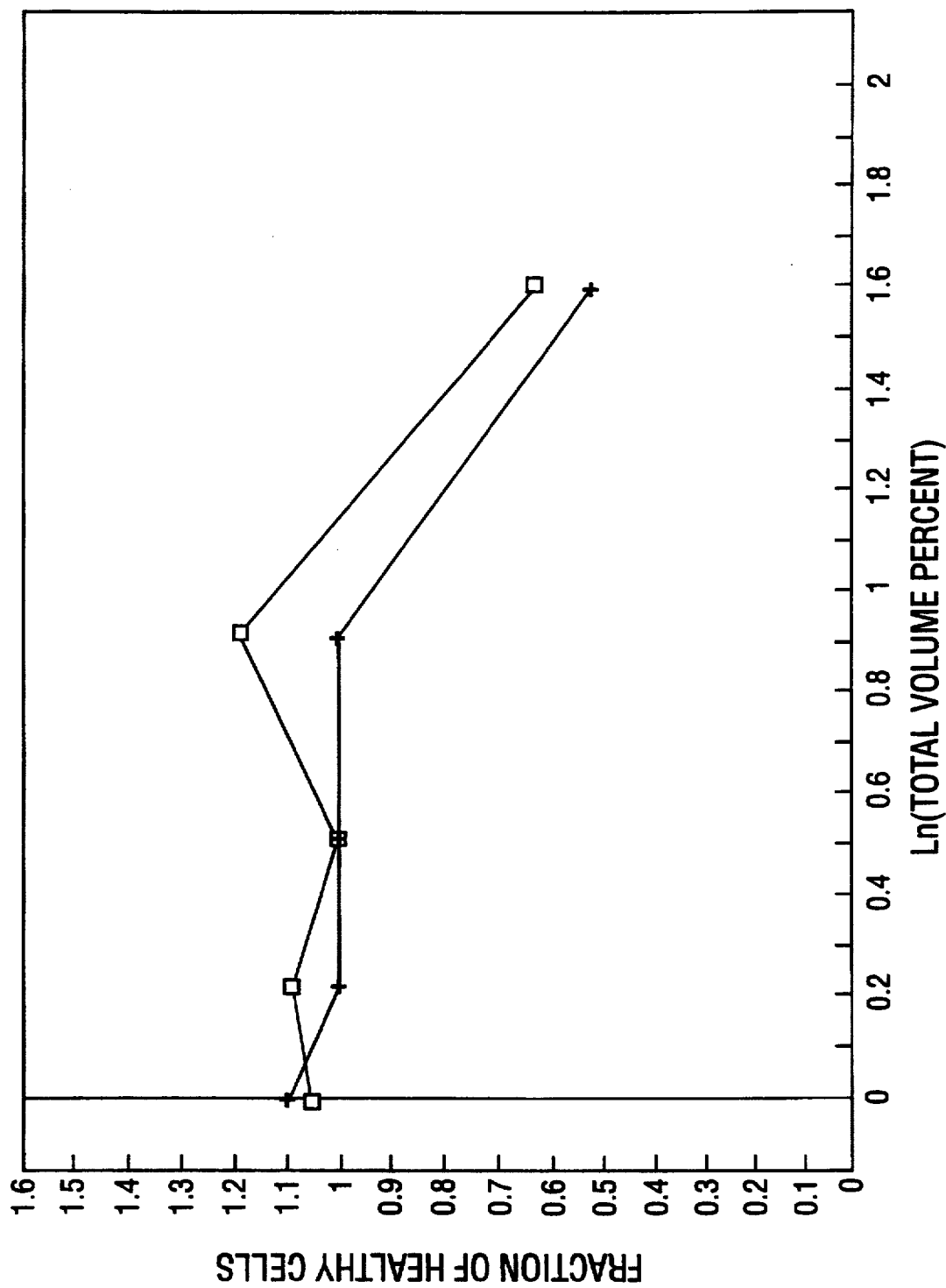
FIG. 6 shows the hemolytic effects of 10% HBCD with and without busulfan on human erythrocytes (□=10% HBCD; +=10% HBCD-BSF).

The hemolytic potential of the various busulfan formulations was evaluated. The data were plotted as fraction of healthy cells versus ln(Total volume percent). Total volume percent is the volume percentage of the vehicle in the mixture after dilution with blood. This has been done in an attempt to simulate the dilution of the preparation in the body after intravenous injection. Healthy erythrocytes were defined as those capable of retaining the hemoglobin inside the cell after mixture with the respective busulfan formulations (Reed et al., 1990). As shown in FIGS. 4–6, all preparations showed similar trends of inducing hemolysis both with and without the addition of busulfan. The addition of busulfan did not add significantly to the overall hemolytic effect. The $LD_{50}$ values of the various vehicle formulations are summarized in Table 6.

TABLE 6

Hemolytic $LD_{50}$ Values of the Various Busulfan Formulations

| Formulation | $LD_{50}$, $(TVP^{a,b})$ |
|---|---|
| 10% HBCD | >6 |
| 10% HBCD-Busulfan | >6 |
| 40% PEG-400 | 10.0 |
| 40% PEG-400-Busulfan | 10.0 |
| 50% PEG-400 | 12.5 |
| 50% PEG-400-Busulfan | 12.5 |
| 20% DMA / 40% PEG-400 | >30 |
| 20% DMA / 40% PEG-400-busulfan | 15.6 |

$^a$TVP = Total Volume Per cent (Reed et al., 1985).
$^b$Each determination was performed in triplicate.

$LD_{50}$ was defined as the total volume percent of the vehicle mixture that is needed to produce 50% hemolysis. Overall, the HBCD preparations had very low $LD_{50}$ values when compared with the PEG formulations.

It has been reported that cyclodextrins have a very high potential for inducing hemolysis (Yoshida et al., 1988), with $LD_{50}$ values of about 2% (w/v). In the present study, however, the HBCD with and without busulfan exerted a minimal hemolytic potential at the vehicle to blood ratios (1:1 to 1:9) studied. The dilution of the respective drug formulation in the actual clinical infusion will be much higher than the highest dilution (1:9) studied. Since there was insignificant hemolysis already at the 1:5 dilution, all formulations presented herein should be safe for parenteral administration. Furthermore, busulfan itself has been shown to cause hemolysis (Bishop et al., 1986); however, in the formulations studied, the contribution of busulfan to overall hemolysis was insignificant.

In Vitro Cytotoxicity of Busulfan.

Figure 10:
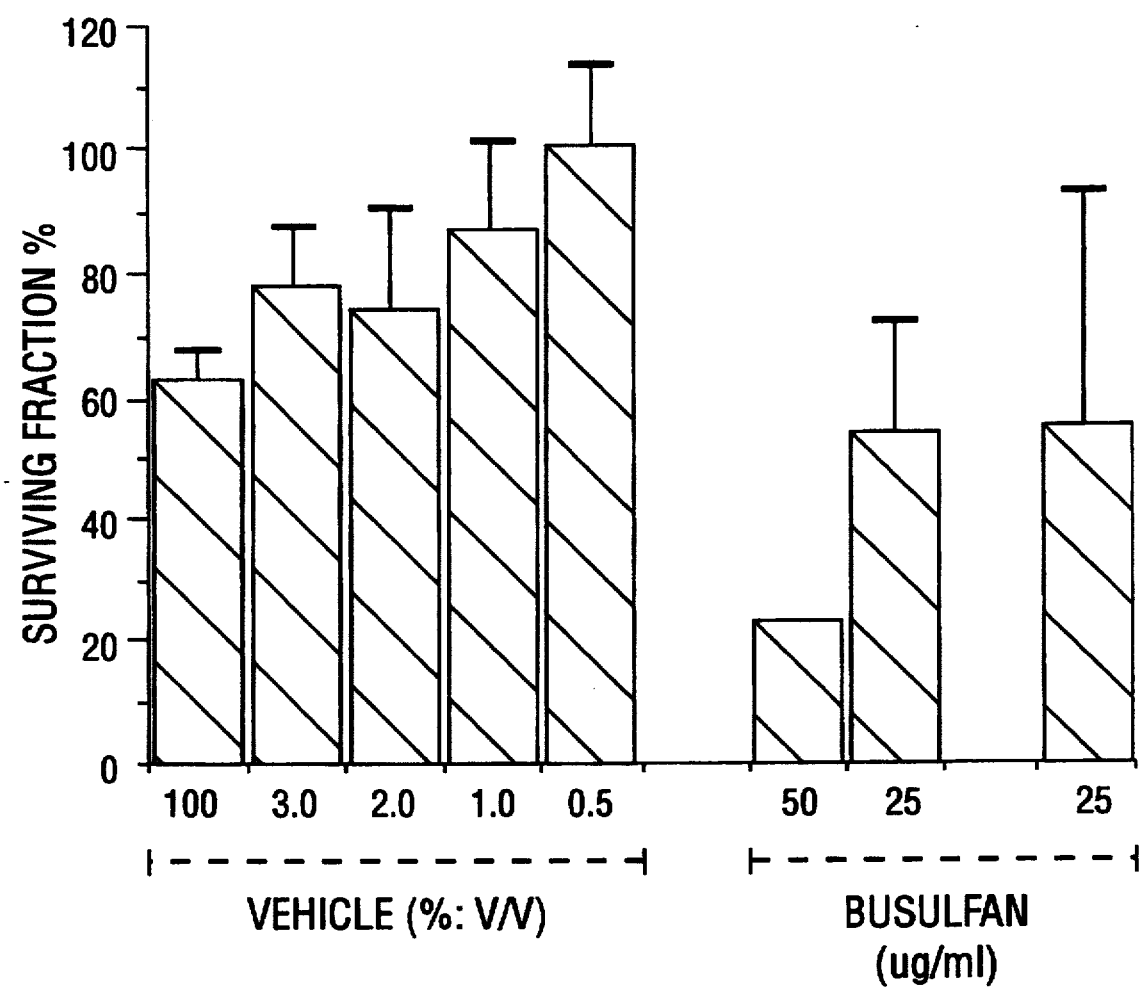
FIG. 10 shows in vitro cytotoxic activity of the DMA:PEG-400 aqueous vehicle on human KBM-3 cells without or with busulfan. KBM-3 cells exposed to busulfan dissolved in a low, non-toxic amount of acetone served as a positive control (last column).

To study the cytotoxic activity of busulfan in the 20% DMA/40% PEG-400 aqueous vehicle, human KBM-3 myeloid leukemia cells (Andersson et al., 1992), were exposed to either the complete vehicle at various concentrations without or with the addition of busulfan for 24 hours at 37° C. The cytotoxicity was assayed with the MTT assay (Hansen et al., 1989). The data show, that the complete vehicle, at high concentrations, exerted some toxicity on its own, likely due to the high osmolarity of this formulation. Busulfan dissolved in this vehicle retained its cytotoxic activity (FIG. 10), such that at 25 µg/ml about 50% of the cells were killed and at 50 µg/ml approximately 80% of the cells were killed. This paralleled the cytotoxicity seen when the cells were exposed to busulfan dissolved in a negligible volume of acetone. The cytotoxic properties of busulfan were retained when the drug was dissolved in the 20% DMA/40% PEG-400 aqueous vehicle.

EXAMPLE 3

Quantitative Extraction of Busulfan from Blood Prior to HPLC, and Pharmacokinetics of i.v. Administered Busulfan The present example provides the development of an efficient technique for extraction of busulfan from blood plasma, adaptation of the HPLC assay for quantitation of busulfan in the plasma extract, and studies of the in vivo plasma pharmacokinetics of busulfan when administered orally as the commercially available tablet, as an oral solution in a vehicle of 40% PEG-400, and as an intravenous injection when dissolved in a vehicle of 40% PEG-400. A comparison of the plasma pharmacokinetics of busulfan in the rat is also given after i.v. busulfan administration. The drug was dissolved at 3 mg/ml in either acetone or DMSO or the complete 20% DMA/40% PEG-400 aqueous solvent.

Quantitative Extraction of Busulfan in Blood Plasma.

Rat plasma (0.2 ml) was spiked with varying concentrations of busulfan (from a stock solution in DMA), to give final drug concentrations of 0.15–3.0 µg/ml. The internal standard, 20 µl, (CGA-112913; in methanol, 20 µg/ml) was then added to the drug-plasma mixtures. After vortexing for 10 seconds, the drug and internal standard were precipitated from the plasma proteins with 0.2 ml acetonitrile with subsequent vortexing for 30 seconds. The busulfan and internal standard were then extracted using 2 ml of ethyl acetate and vortexed for 1 minute. The solutions were centrifuged for 10 minutes and 1 ml of the ethyl acetate layer was evaporated to dryness under compressed air. The busulfan and internal standard were then dissolved in 0.5 ml of distilled water and derivatized with 0.2 ml of an 8.2% (w/v) solution of diethyldithiocarbamic acid sodium and vortexed for 30 seconds.

The busulfan derivative, DDCB (Diethyldithiocarbamoyl butane), was subjected to solid phase extraction with Sep-Pak LC ™ cartridges (Millipore Corporation, Bedford, Ill.) under vacuum. The cartridges were conditioned with three 1-ml washes of methanol followed by two 1-ml washes with distilled water. The derivatized solutions were then passed through the cartridges and the cartridges washed twice with 1 ml 50% methanol in distilled water. The DDCB and the internal standard were eluted from the columns using 250-µl methanol twice, followed by two washes of 0.5-ml of ethyl acetate. The combined extracts were evaporated to dryness with compressed air and reconstituted with 0.2 ml of the mobile phase (acetonitrile: water: THF, 55: 25: 20% (v/v, pH 4.2). The reconstituted extracts were stored at 4° C. overnight and then subjected to HPLC analysis. In these experiments the assay-1 from Table 2 was used. Assay-1 provided better resolution with the acetonitrile/water/THF than that obtained with methanol/water as the mobile phase in assay-2. CGA-112913 is a suitable internal standard for assay-1. Ten µl of the stock solution of CGA-112913 in acetonitrile was added to each sample as internal standard and 40 to 60 µl of sample was injected into the HPLC for analysis.

Pharmacokinetic Studies in Animals: Experimental Protocol.

The pharmacokinetic studies were conducted in Sprague-Dawley rats (300–350 g) (Sasco Corp., Lincoln, Nebr.). The animals were anesthetized using intraperitoneal injections of pentobarbital sodium (50 mg/kg body weight) (Nembutal TM Sodium Solution, Abbott Laboratories, North Chicago, Ill.). The jugular veins were cannulated percutaneously from the back of the neck, and the cannulas were kept patent with heparinized saline. All animals were allowed to recover for 24 hours after cannulation before the pharmacokinetic studies were commenced. The studies were conducted to determine the plasma pharmacokinetics of busulfan after the administration of drug as:

(1) The commercially available tablet (2 mg/tablet, Burroughs Welcome Pharmaceuticals, London, UK). In the second experimental series the tablet preparation was administered to animals that had either had free access to food and water or that had been fasting for at least four hours.

(2) 40% PEG400-busulfan as an oral solution.

(3) 40% PEG400-busulfan administered as an i.v. injection.

(4) 20% DMA/40% PEG-400/aqueous solution administered as an i.v. injection.

(5) 100% acetone used as the sole solvent.

(6) 100% DMSO used as the solvent; the busulfan was dissolved in DMSO immediately prior to i.v. administration, due to its propensity to rapidly degrade in this vehicle.

One rat was used for each administration form. All animals were allowed free access to food and water, unless specified where the pharmacokinetics were compared in fasting and freely eating animals after administration of the busulfan tablet. The drug was given at a dose of 1 mg/kg body weight in all instances. When given orally, the tablet was crushed and the dose equivalent of 1 mg/kg was administered via an oro-gastric catheter. The oral 40%-PEG400-busulfan solution was administered to the animals similar to the tablets.

The parenteral 40%-PEG400-busulfan solution and the DMA/PEG-400/aqueous solution were given i.v. through the jugular cannula. The cannula and tubing were carefully flushed with heparinized saline after the injection to prevent drug from adhering to the catheter walls and subsequently interfering with the blood sampling and pharmacokinetic analysis.

After the drug administration, 0.5 ml blood samples were withdrawn at defined time intervals (at 0, 2, 5, 10, 30, 60 min, and at 2, 4, 6, and 8 hours), via the jugular catheters. The removed blood volume was replaced by an equal volume of saline. The samples were transferred to microcentrifuge tubes and immediately centrifuged at 13,000 r.p.m. for 60 sec. The plasma fraction was then aspirated and stored at $-20°$ C. until extracted for HPLC assay.

Pharmacokinetic Data Analysis.

The pharmacokinetic parameters were calculated from the obtained plasma concentration vs. time profiles after administration of the respective preparations as described (Benet et al., 1985; Gibaldi et al., 1975; Nilsson et al., 1981). Thus, the elimination rate constant was obtained from the slope of the Ln (concentration) vs. time profile. The area under the concentration vs. time curve (AUC) was calculated using the linear trapezoidal rule. The following equations were used to calculate the various pharmacokinetic parameters:

$$V = X_0/C_0 \quad \text{(Eq. 1)}$$

$$Cl = V \times K \quad \text{(Eq. 2)}$$

$$t_\frac{1}{2} = 0.693/K \quad \text{(Eq. 3)}$$

$$F = Cl \times AUC/DOSE \quad \text{(Eq. 4)}$$

V = Volume of distribution
$X_0$ = Dose,
$C_0$ = Plasma concentration at time = 0,
Cl = Systemic Clearance,
K = Elimination rate constant,
$t_\frac{1}{2}$ = half life,
F = Bioavailability,
AUC = Area under the plasma concentration vs. time curve.

RESULTS AND DISCUSSION

HPLC Assay of Busulfan in Plasma.

The retention times of DDCB and the internal standard (CGA-112913) in the HPLC assay were 7.5 and 8.4 min. respectively. The initial drug extraction from plasma with acetonitrile and ethyl acetate was essential to recover all drug from the plasma and to avoid interference from endogenous plasma (protein) components. Without this extraction, a large endogenously-derived peak completely obscured the DDCB peak. The recovery of derivatized busulfan (DDCB) with the above described technique was 98.8% with an accuracy of 8.9% and a limiting sensitivity in the linear interval of 100-150 ng/ml.

A standard curve was prepared in the concentration range of 150 -1,500 mg/ml and a good correlation was obtained between the (known) plasma busulfan concentration and peak height ratios (PHR);

$$PHR = 0.1623 \times (\text{busulfan concentration}) + 0.751,$$
$$r^2 = 0.98 \quad \text{(Eq. 5)}$$

Pharmacokinetic Studies.

In the first experimental series only the plasma pharmacokinetic properties of busulfan after oral administration (tablet; non-fasting animal) and parenteral dosing (40%-PEG400-busulfan; non-fasting animal) were investigated. In the second series a complete study of the plasma pharmacokinetics of busulfan after administration of all the preparations as described above was conducted.

Figure 8:
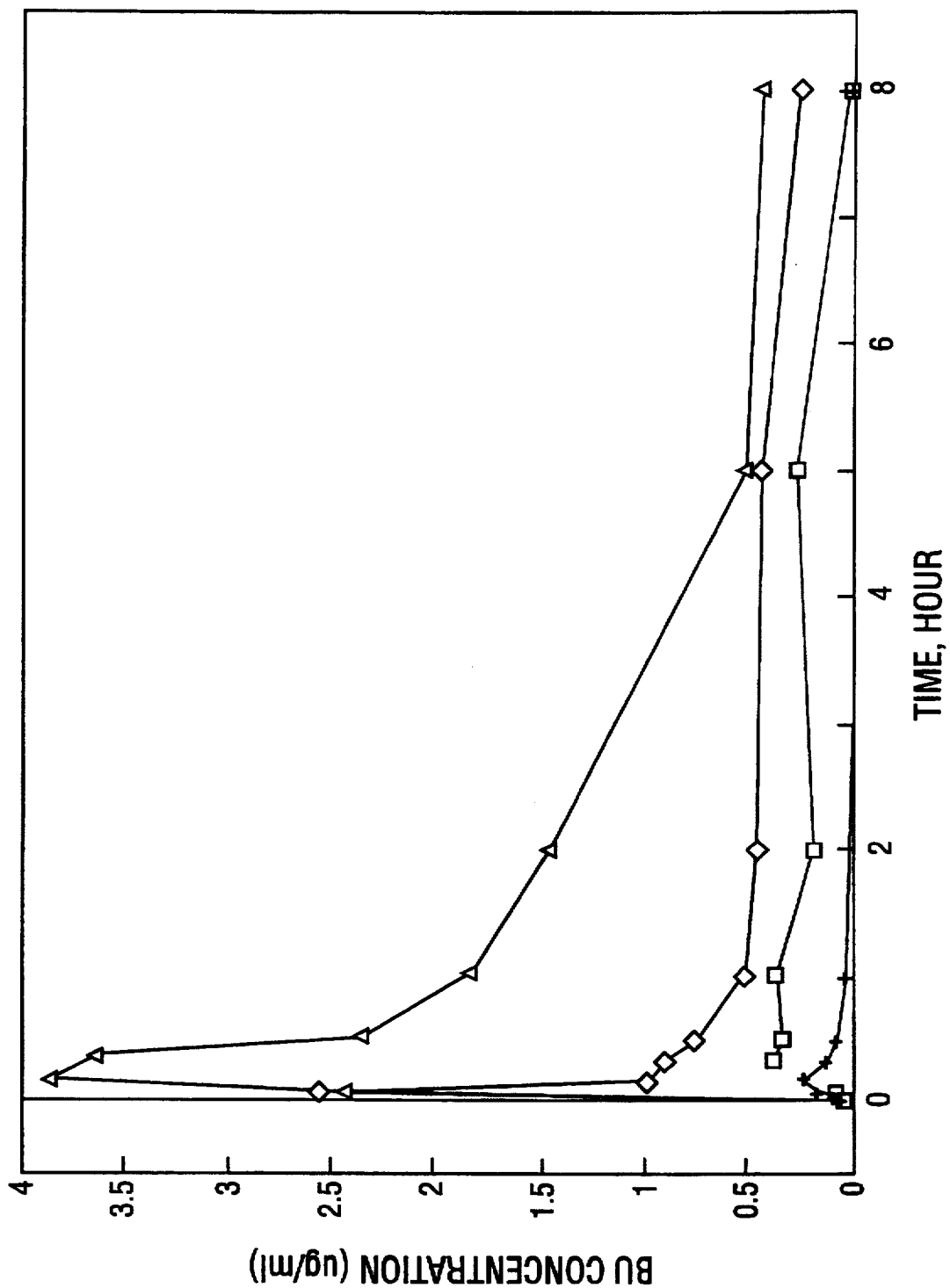
FIG. 8 shows comparative plasma profiles of busulfan. The drug was administered to fasting or non-fasting rats as tablets, as an oral solution in 40% PEG-400, or as an i.v. bolus of busulfan in 40% PEG-400 (□=tablet; +-=tablet, fasting; ◇=oral solution;△-i.v. solution).
Figure 9:
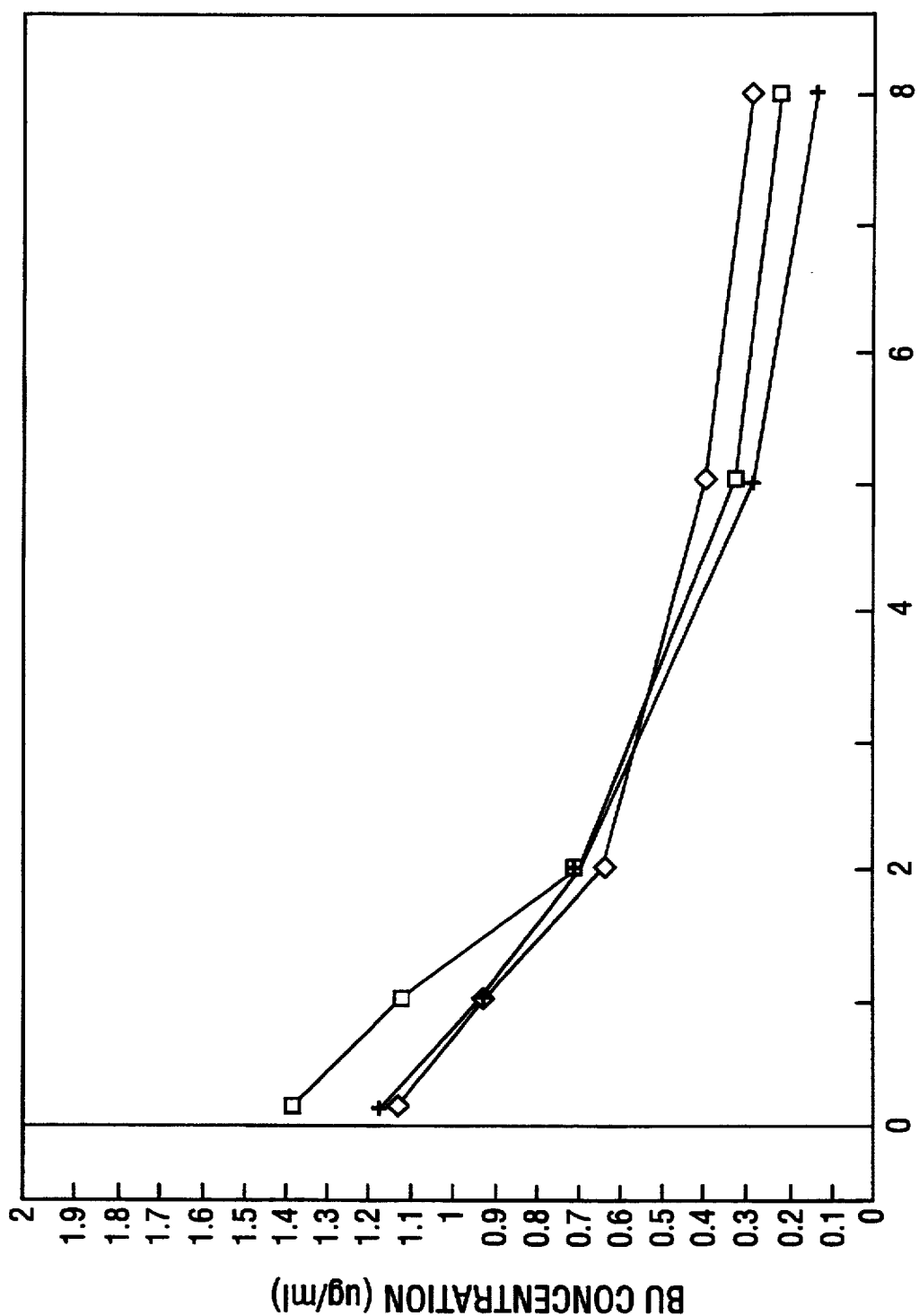
FIG. 9 shows the plasma concentration profiles in rats of i.v. administered busulfan dissolved at 3 mg/ml in acetone or in DMSO or in the 20% DMA/40% PEG-400 aqueous vehicle. The total volume injected was 100-150 μL and the dose of busulfan was 1 mg/kg body weight. All solutions were prepared fresh immediately prior to administration (□=acetone; +=DMSO; ◇=20DMA:40% PEG-400:40% water).

The plasma busulfan concentrations vs. time profiles of the different preparations and routes of administration were plotted (FIGS. 8 and 9, and Tables 7 and 8).

TABLE 7

Busulfan Plasma Conc. (μg/ml) After Administration of 1 mg/kg

| Time (hr) | A | B | C | D |
|---|---|---|---|---|
| 0.000 | 0.034 | 0.000 | 0.000 | 0.000 |
| 0.083 | 0.074 | 0.158 | 2.552 | 2.447 |
| 0.166 | N/A | 0.223 | 0.994 | 3.858 |
| 0.333 | 0.377 | 0.119 | 0.896 | 3.645 |
| 0.500 | 0.327 | 0.073 | 0.752 | 2.344 |
| 1.000 | 0.369 | 0.041 | 0.509 | 1.845 |
| 2.000 | 0.195 | 0.016 | 0.462 | 1.489 |
| 5.000 | 0.286 | 0.000 | 0.450 | 0.534 |
| 8.000 | 0.042 | 0.000 | 0.305 | 0.471 |

Group:
A = oral tablet, non-fasting
B = oral tablet, fasting
C = 40%-PEG400-busulfan, oral solution
D = 40%-PEG400-busulfan, parenteral solution In FIG. 9 and Table 8, the busulfan concentration vs. time profiles and the resulting pharmacokinetic parameters resulting from 3 different formulations for i.v. administration in a murine model are shown. After in vivo administration of the busulfan dissolved in acetone or DMSO, significant hemolysis occurred, although no obviously serious adverse effect(s) were recorded. These formulations yielded comparable pharmacokinetic data to those obtained with the 20% DMA/40% PEG-400 aqueous vehicle.

TABLE 8

Plasma Concentrations of Busulfan in Rats[a]

| time (hours) | BUSULFAN CONCENTRATION (μg/ml) | | |
|---|---|---|---|
| | ACETONE | DMSO | DMA/PEG-400[b] |
| 0.166 | 1.384 | 1.166 | 1.135 |
| 1.000 | 1.120 | 0.937 | 0.923 |
| 2.000 | 0.707 | 0.707 | 0.640 |
| 5.000 | 0.319 | 0.268 | 0.388 |
| 8.000 | 0.216 | 0.140 | 0.282 |

[a] = Busulfan was administered i.v. at a dose of 1 mg/kg body weight in a total volume of 100–150 μl.
[b] = DMA:PEG-400:Water (20:40:40% v/v)
All three solvent systems contained 3 mg/ml busulfan As expected, the resulting plasma concentrations were higher after parenteral administration than after oral dosing. Interestingly, the proposed vehicle for parenteral administration appears to also facilitate the intestinal absorption of busulfan when used for oral administration. Further, non-fasting animals seem to absorb more drug than fasting subjects, however this needs to be studied in a larger number of animals to exclude incidental inter-animal variation as the source for this observed alteration in bioavailability. It may suggest, however, that the low pH in the stomach contributes significantly to degradation of the busulfan prior to its absorption from the intestinal tract to the blood stream. After parenteral drug administration, the resulting peak plasma concentration of busulfan was approximately ten times higher and the AUC about five times higher than those seen after the standard tablet formulation in non-fasting animals. The higher bioavailability yielded by the parenteral administration form can be expected to parallel a higher reproducibility of systemically available drug after parenteral vs. the standard oral (tablet) formulation (Table 9 and 10).

TABLE 9

| Parameter | Pharmacokinetic Parameters of Busulfan | | | |
|---|---|---|---|---|
| | A | B | C | D |
| K (h^-1) | 0.275 | N/A | 0.166 | 0.268 |
| t₁ (hr) | 2.513 | N/A | 4.169 | 2.581 |
| AUC (μg × hr/ml) | 1.927 | 0.124 | 4.987 | 10.501 |
| $C_{max}$ (μg/ml) | 0.377 | 0.223 | 2.552 | 3.858 |
| $t_{max}$ (min) | 20.00 | 10.00 | 5.000 | 10.00 |

A = oral tablet, non-fasting
B = oral tablet, fasting
C = 40%-PEG400-busulfan, oral solution
D = 40%-PEG400-busulfan, parenteral solution

TABLE 10

| PARAMETER | Pharmacokinetic Parameters of Busulfan[a] | | |
|---|---|---|---|
| | ACETONE | DMSO | DMA/PEG-400[b] |
| K (h^-1) | 0.243 | 0.278 | 0.205 |
| t₁ (h) | 2.852 | 2.495 | 3.379 |
| AUC (μg.hr/ml) | 5.605 | 4.706 | 5.421 |
| CL (ml/hr) | 60.658 | 67.997 | 46.118 |

[a] = Busulfan was administered i.v. at a dose of 1 mg/kg body weight in a total volume of 100–150 μL
[b] = DMA:PEG-400:water (20:40:40%, v/v), in all solvents there was 3 mg/ml of busulfan his clinically translates into a more predictable, and accurately reproducible cytotoxic effect as well as better control over the side effects and, therefore a higher degree of safety after busulfan-based chemotherapy.

The available data emphasize the importance of introducing a reliable parenteral busulfan formulation for achievement of highly reproducible antitumor therapy with predictable cytotoxicity and maximum safety to the patient.

EXAMPLE 4

Treatment of Malignancy in an Animal Using Parenterally Administered Busulfan

The present example illustrates use of chemically stable parenterally administered formulations of busulfan for the treatment of malignant disease in an animal. The animal studies serve as model systems for exploring optimal administration schedule(s) for subsequent use of parenteral busulfan formulations in the clinical treatment of human neoplasms with therapy based on this parenteral preparation alone or in combination with other cytotoxic agent(s).

Methodology.

In order to determine the proper procedures for human treatment, the following studies are carried out.

1. The dose-linearity of parenteral busulfan as compared to p.o. busulfan in the rat is first determined.
2. The second step is the establishment of chimerism and the development of graft-versus-host disease in the rat using high-dose parenteral busulfan in combination with other immunosuppressive therapy such as e.g. cyclophosphamide for conditioning, prior to allogeneic transplantation of (partially mis-) matched marrow, using syngeneic marrow transplants as the controls. The technique has been described (Santos G. W. and Tutschka P. J., 1974; Tutschka, P. J. and Santos G. W. 1975; Oaks M. K. and Cramer D. V. 1985).
3. The third step is the use of parenteral busulfan for the eradication of established experimental systemic cancer, such as leukemia in the L1210 mouse (NCI monograph, 1977) and in the Brown Norway Rat (Hagenbeek A, 1977). Hemopoietic cell rescue is provided by administering litter-mate derived (syngeneic) marrow to protect from bone marrow suppression after the parenteral busulfan therapy. This allows a detailed investigation of extramedullary dose-limiting toxicity of the parenteral formulation. Further, by using graded doses of malignant cells administered to the animals prior to delivering high-dose busulfan, the relative merits of various dose schedules can be calculated in a (semi-)quantitative fashion, to optimize administration schedule intended for clinical use.
4. Clinical phase one-two studies of parenteral busulfan for the treatment of disseminated malignant disease in man is the next step. Patients with advanced forms of lymphoma, breast cancer and leukemia are targeted. The busulfan therapy is delivered as part of combination therapy using two (or more) alkylating agents, e.g. busulfan in combination with cyclophosphamide and/or etoposide, followed by hemopoietic cell rescue with either autologous or allogeneic marrow as described using oral busulfan (Santos G. W. et al., 1983; Thomas, E. D. 1987; Copelan E. A. et al., 1987, and reviewed by Giralt and Andersson, 1993).
5. Alternatively, using the intraarterial route of administration, regional perfusion of localized solid tumors, such as tumors that are localized to a limb, as well as those that are confined to a well defined area of a visceral organ such as the liver, can now be accomplished using busulfan. Although this technique itself is not new (Stehlin et al., 1975; McBride, C. M., et al., 1975; Schraffordt K., et al., 1977), the employment of busulfan in this treatment modality has been hampered by the lack of a busulfan formulation that could be safely administered and which retains its cytotoxic activity throughout the period of treatment. Such investigations have to be performed as clinical phase one-two studies, since there is no appropriate animal model of regional therapy. Due to the expected low-to moderate systemic side effects of such therapy, the need for hemopoietic support would be limited to (at most) the administration of recombinant hemopoietic growth factor(s), possibly in addition to blood products. This is in contrast to the above outlined studies (2-4) which would necessitate administration of marrow and/or peripheral blood progenitor cells, to ensure rapid hemopoietic reconstitution.

A dose range for parenteral administration of busulfan for an animal such as a rat may be from 0.15 to 50 mg/kg with or without cyclophosphamide. The dose may be administered as a bolus or divided into three portions. A method of treatment of an individual using busulfan as a chemotherapeutic agent may involve intra-arterial or intravenous administration at a dose range of 0.05-2.0 mg/kg body weight every 6-12 hours for 3-5 days. A phase I study may include the administration of divided doses spaced 6 hours part.

The following references are incorporated in pertinent part by reference herein for the reasons cited above.

REFERENCES

Abe T.: 1975, *Jpn J. Clin. Hematol.* 16:839-849.
Albrecht M. et al., 1971, *Med. Klin.*, 66 (4):126-130.
Ambs V. E. et al., 1971, *Arch. Kinderheilk* 182:218-239.
Andersson B. S., et al., 1992, *Exp. Hematol.*, 20:361-36
Bhagwatwar, H., et al., 1993, *Abstract for American Association for Cancer Research*, May 19-23,1993
Benet L. Z., and Sheiner L. B.,*Pharmacokinetics: The dynamics of drug absorption, distribution, and elimination.* In: *The pharmacological basis of therapeutics.*: 1985 Goodman et al. (Eds.) 7th Ed., MacMillan Publishing Company Inc. New York, N.Y., pp. 3-34.
Bishop J. B. and Wassom J. S., 1986, *Mutation Res.* 168:15-45.
Blume K. G. and Forman S. J., 1987, *Blut* 55:49-53.
Buckner C. D. et al., 1992, *Blood* 80:277 (Abstr.).
Buckner C. D. et al., 1975, *Scand J. Hematol.* 3:275-288.
Canellos G. P., Chronic Leukemias. In: *Cancer: Principles and Practice of Oncology*, 2nd Edition. 1985, DeVita V. T. Jr. et al., (Eds.). J. B. Lippincott Co. Philadelphia, Pa. pp. 1739-1752.
Champlin R. C. et al., 1985, *Transplant. Proc.* 17:496-499.
Collis C. H., 1980, *Cancer Chemother. Pharmacol.* 4:17-27.
Copelan E. A. et al., 1989, *Br. J. Haematol.* 71:487-491.
Galton D. A. G., 1953, *Lancet* 1:208-213.
Ganda O. P. and Mangalik A., 1973, *J. Assoc. Physcns. India*, 21(6):511-516.
Geller R. B. et al., 1989, *Blood*, 73:2209-2218.
Gibaldi M. and Perrier E. D., 1975, Pharmacokinetics. Marcel Dekker Publishers, New York, N.Y.
Giles, A. R., et al., 1984, *Br. J. Haematol.*, 57:17-23 Abstract
Giralt S. and Andersson B. S., 1993, *Oncology*, InPress.
Grigg A. P. et al., 1989, *Ann. Intern. Med.* 111:1049-1050.
Grochow L. B. et al., 1989, Cancer *Chemother. Pharmacol.* 25: 55-61.
Haddow A. and Timmis G. M., 1953, *Lancet* 1:207-208.
Hagenbeek A., 1977, *Leuk. Res.*, 1:85-90.
Hagenbeek A. et al., 1977, *Leukemia Research* 1:99-101.
Hansen M. B., et al., 1989, *J. Immunol. Methods*, 119:203-210.
Hassan, M., et al., 1992, *Cancer Chemotherapy and Pharmacology*, 30:81-85.
Hughes T. P. and Goldman J. M., Chronic myeloid leukemia. In: *Hematology, Basic principles and practice.* 1991, Hoffman R. et al., Churchhill Livingstone Inc., New York, N.Y. pp. 854-869.
Keating M. J. et al., 1993, *Leukemia and Lymphoma*, In Press. Kitamura, Y., et al., 1979, *Jpn. J. Anesthesiol.* 28:512-517 Abstract
Koch H., and Lesch R., 1976, *Med. Welt*, 27(7):308-311.
Lu C. et al., 1984, *Cancer Treatm. Repts.* 68: 711-717.
McBride C. M. et al., 1975, *Ann Surg.* 182:316-324.
MacKicham J. J. and Bechtel T. P., 1990, *J. Chromatography*, 532:424-428.
Mann H. B. and Whitney D. R., 1947, *Ann. Math. Statist.* 18:50-60.
Marcus R. E. and Goldman J. M., 1984, *Lancet II* (8417-18) 1463.
Martell R. W. et al., 1987, *Ann. Intern. Med.* 106:173.
Merck Index, 11th Ed., 1989, Budaveri, S., et al., eds. *Propyleneglycol,* p. 7870, Merck & Co., Inc., Rahway, N.J.
Miller C. et al., 1991, *Blood* 78:1155 (Abstr.).
National Cancer Institute Monograph 45, 1977, USA-USSR Monograph, *Methods of Development of New Anticancer Drugs DHEW* Publication No. (NIH) 76-1037:147-153.
Nilsson S. O. et al., 1981, *Cancer Chemother. Pharmacol.* 5:261-266.
Oakhill A. et al., 1981, *J. Clin. Pathol.* 34 (5): 495-500.
Oaks M. K. and Cramer D. V., 1985, *Transplantation* 39:69-76.
Peters W. P. et al., 1987, *Cancer Res.*, 47:6402-6404.
Reed K. W. and Yalkowsky S. H., 1985, *J. Parenteral Sci. Techn. 39* (2): 64-68.
Sanders J. E. et al., 1988, *Bone Marrow Transplantation* 3:11-19.
Santos G. W. et al., 1983, *N. Engl. J. Med.* 309:1347-1353.
Santos G. W. and Tutschka, P. J., 1974, *J. Natl. Cancer Inst.* 53:1781-1785.
Schraffordt K. H. et al., 1977, *Cancer* 39:27-33.
Schwertfeger R. et al., 1992, *Blood* 80:2125 (Abstr.).
Sharkis, S. J. and Santos, G. W., 1977, *Leukemia Research* 251-252.
Sheridan W. P. et al., 1989, *Med. J. of Australia* 151:379-386.
Stehlin J. S. et al., 1975, *Surg. Gynecol. Obstet.* 140:339-348.
Sureda A. et al., 1989, *Ann. Intern. Med.* 111:543-544.
Thomas E. D., 1987, *American H of The Medical Sciences* 294:75-79.
Tutschka P. J. et al., 1987, *Blood*, 70:1382-1388.
Tutschka P. J. and Santos G. W., 1975, *Transplantation* 20:101-106.
Vassal G. et al., 1990, *Cancer Res.* 50:6203-6207.

Vaughn W. P. et al., 1991, *Bone Marrow Transplantation* 8:489–496.

Weiss A. J. et al., 1962, *Cancer Chemotherapy Rep.* 16:477–485.

Yeager A. M. et al., 1986, *New Engl. J. Med.* 315:141–147.

Yoshida A. et al., 1988, *Int. J. Pharmaceutics*, 46:217–222.

It is understood that the examples and embodiments described herein are for illustrative purposes only and that various modifications in light thereof will be suggested to persons skilled in the art and are to be included within the spirit and purview of this application and scope of the appended claims.

What is claimed is:

1. A pharmaceutically acceptable formulation for intravascular administration of busulfan comprising busulfan dissolved at a concentration of about 1–19 mg/ml in a liquid mixture comprising water and about 10–70% of at least one miscible, physiologically acceptable, busulfan solvent selected from the group consisting of N',N-dimethylacetamide, polyethylene glycol, propylene glycol, glycerin cyclodextrin and hydroxypropylbetacyclodextrin.

2. A method for treating malignant disease responsive to busulfan in an individual comprising intravascular administration of a pharmaceutically effective amount of the formulation of claim 1.

3. The method of claim 2 where the administration is intravenous.

4. The method of claim 2 wherein the water miscible, physiologically acceptable, busulfan solvent is N',N-dimethylacetamide.

5. The method of claim 4 wherein N',N-dimethylacetamide is at a concentration of 5% to 70%.

6. The method of claim 2 wherein the busulfan solvent is an aqueous polyethyleneglycol solution.

7. The method of claim 6 wherein polyethyleneglycol is at a concentration of about 5% to 50%.

8. The method of claim 6 wherein the polyethyleneglycol has a molecular weight between 200 and 2000.

9. The method of claim 6 wherein the polyethyleneglycol has a molecular weight between 350 and 450.

10. The method of claim 2 wherein the water miscible, physiologically acceptable, busulfan solvent is a mixture of N',N-dimethylacetamide and an aqueous carrier solution allowing busulfan solubility and stability.

11. The method of claim 10 wherein the aqueous carrier solution allowing busulfan solubility and stability is a polyethyleneglycol solution.

12. The formulation of claim 8 wherein the water miscible, physiologically acceptable, busulfan solvent is N',N-dimethylacetamide.

13. The formulation of claim 12 wherein N',N-dimethylacetamide is at a concentration of 5% to 7%.

14. The formulation of claim 11 wherein the water miscible, physiologically acceptable, busulfan solvent is polyethyleneglycol.

15. The formulation of claim 14 wherein polyethyleneglycol is at a concentration of 5% to 50%.

16. The formulation of claim 14 wherein the polyethyleneglycol has a molecular weight between 200 and 2000.

17. The formulation of claim 14 wherein the polyethyleneglycol has a molecular weight between 350 and 450.

18. The formulation of claim 8 wherein the water miscible, physiologically acceptable, busulfan solvent is a mixture of N',N-dimethylacetamide and an aqueous carrier solution allowing busulfan solubility and stability.

19. The formulation of claim 18 wherein the aqueous carrier solution allowing busulfan solubility and stability is a polyethyleneglycol solution.

20. The formulation of claim 8 wherein the water miscible, physiologically acceptable, busulfan solvent is propylene glycol.

21. The formulation of claim 1 wherein the water miscible, physiologically acceptable, busulfan solvent is an aqueous solution of hydroxypropylbetacyclodextrin.

22. A pharmaceutically acceptable formulation for intravascular administration of busulfan comprising about 1–7.5 mg/ml dissolved busulfan, 35–45% polyethyleneglycol-400, water and 5–15% N',N-dimethylacetamide.

23. A pharmaceutically acceptable formulation for intravascular administration of busulfan comprising about 1–10 mg/ml dissolved busulfan, 35–45% polyethyleneglycol-400, water and 15–25% N',N-dimethylacetamide.

24. A method for treating a patient for a malignant condition responsive to busulfan, the method comprising:
obtaining an intravascularly administrable busulfan preparation; and
intravascularly administering said preparation to the patient in an amount effective to treat said condition.

25. The method of claim 24 wherein the malignant condition is a localized solid tumor and the intravascular administration is intraarterial to regionally perfuse said solid tumor.

26. A method for treating leukemia or a lymphoma in a patient undergoing a bone marrow transplant, the method comprising:
obtaining an intravenously administrable busulfan preparation; and
intravenously administering said preparation to the patient having leukemia or a lymphoma in an amount conditioning the patient for the bone marrow transplant.

27. The method of claim 24, or 26 wherein the amount of busulfan administered is from about 0.01 to 1 mg/kg every 6 hours.

28. The method of claim 24, or 26 wherein the preparation is the formulation of claim 15.

29. The method of claim 28 wherein the malignant condition is a breast cancer, leukemia or a lymphoma.

30. The method of claim 29 wherein the leukemia is acute myelogenous leukemia.

31. The method of claim 29 wherein the leukemia is chronic myelogenous leukemia.

* * * * *

UNITED STATES PATENT AND TRADEMARK OFFICE
CERTIFICATE OF CORRECTION

PATENT NO.   : 5,430,057
DATED        : July 4, 1995
INVENTOR(S)  : Borje S. Andersson et al.

It is certified that error appears in the above-indentified patent and that said Letters Patent is hereby corrected as shown below:

On the title page, item [75] delete the initials "S. L." and insert the name --Shu-Lian--therefor.
In claim 1, column 21 line 24, insert the mark --,-- immediately after the word 'glycerin'.

In claim 12, column 21, line 54, delete the numeral "8" and insert the numeral --1-- therefor.

In claim 13, column 21, line 58, delete the numeral "7" and substitute the numeral --70-- therefor.

In claim 14, column 21, line 59, delete the numeral "11" and substitute the numeral --1-- therefor.

In claim 18, column 22, line 7, delete the numeral "8" and substitute the numeral --1-- therefor.

In claim 20, column 22, line 15, delete the numeral "8" and substitute the numeral --1-- therefor.

In claim 28, column 22, line 56, delete the numeral "15" and substitute the numeral --1-- therefor.

Signed and Sealed this

Eighteenth Day of June, 1996

*Attest:*

BRUCE LEHMAN

*Attesting Officer*     *Commissioner of Patents and Trademarks*